(12) United States Patent
Bangera et al.

(10) Patent No.: US 8,845,969 B2
(45) Date of Patent: Sep. 30, 2014

(54) MATERIAL, SYSTEM, AND METHOD THAT PROVIDE INDICATION OF A BREACH

(75) Inventors: Mahalaxmi Gita Bangera, Renton, WA (US); Michael H. Baym, Cambridge, MA (US); Roy P. Diaz, Seattle, WA (US); Roderick A. Hyde, Redmond, WA (US); Muriel Y. Ishikawa, Livermore, CA (US); Edward K. Y. Jung, Bellevue, WA (US); Jordin T. Kare, Seattle, WA (US); Erez Lieberman, Cambridge, MA (US); Nathan P. Myhrvold, Medina, WA (US); Dennis J. Rivet, Chesapeake, VA (US); Michael A. Smith, Phoenix, AZ (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 618 days.

(21) Appl. No.: 13/135,369

(22) Filed: Jun. 30, 2011

(65) Prior Publication Data

US 2012/0133504 A1     May 31, 2012

Related U.S. Application Data

(63) Continuation of application No. 12/927,968, filed on Nov. 29, 2010, now Pat. No. 8,715,576, which is a continuation-in-part of application No. 12/927,972, filed on Nov. 29, 2010, now Pat. No. 8,501,103.

(51) Int. Cl.
*G05B 9/00*     (2006.01)
*G08B 21/24*     (2006.01)
*G01N 31/22*     (2006.01)

(52) U.S. Cl.
CPC ............ *G01N 31/223* (2013.01); *G08B 21/245* (2013.01)
USPC ............................ 422/117; 422/119; 340/540

(58) Field of Classification Search
CPC ........ G08B 23/00; G08B 21/00; G08B 21/02; G08B 1/08; A61B 19/04; A61B 19/041
USPC ..................... 340/540, 531, 571, 572.1, 604; 422/117, 119
See application file for complete search history.

(56) References Cited

U.S. PATENT DOCUMENTS

| | | |
|---|---|---|
| 4,234,907 A | 11/1980 | Daniel |
| 5,157,379 A | 10/1992 | Dennison |

(Continued)

OTHER PUBLICATIONS

Briand et al.; "Integration of MOX gas sensors on polyimide hotplates"; Sensors and Actuators B: Chemical; 2008; pp. 430-435; vol. 130, No. 1.

(Continued)

*Primary Examiner* — Eric M Blount

(57) ABSTRACT

A multilayer material is described herein that includes at least one signaling layer configured to propagate at least one electromagnetic signal; and a flexible layer configured to enclose the at least one signaling layer, wherein the flexible layer is substantially impermeable to an environment and to the at least one electromagnetic signal. The multilayer material including the at least one signaling layer is configured to transmit a change in the at least one electromagnetic signal upon exposure of the signaling layer to the environment. A system, an article of clothing, or a method is described herein.

37 Claims, 4 Drawing Sheets

(56) References Cited

U.S. PATENT DOCUMENTS

| | | | |
|---|---|---|---|
| 5,335,373 | A | 8/1994 | Dangman et al. |
| 5,430,434 | A | 7/1995 | Lederer et al. |
| 5,448,177 | A | 9/1995 | Thompson |
| 5,549,924 | A | 8/1996 | Shlenker et al. |
| 5,567,932 | A | 10/1996 | Staller et al. |
| 5,734,323 | A | 3/1998 | Hermes et al. |
| 5,911,848 | A | 6/1999 | Haber et al. |
| 5,976,881 | A | 11/1999 | Klingner |
| 6,060,986 | A | 5/2000 | Lederer |
| 6,323,577 | B1 | 11/2001 | Inoue et al. |
| 6,347,408 | B1 | 2/2002 | Yeh |
| 6,395,383 | B1 | 5/2002 | Maples |
| 6,841,601 | B2 | 1/2005 | Serpico et al. |
| 6,850,162 | B2 | 2/2005 | Cacioli et al. |
| 6,851,844 | B2 | 2/2005 | Guy |
| 6,995,353 | B2 | 2/2006 | Beinhocker |
| 7,225,476 | B2 | 6/2007 | Cerbini et al. |
| 7,630,591 | B2 | 12/2009 | Allen et al. |
| 7,683,797 | B2 | 3/2010 | Woodard et al. |
| 7,927,558 | B2 | 4/2011 | Kirollos et al. |
| 7,993,606 | B2 | 8/2011 | Trentacosta et al. |
| 8,323,577 | B2 | 12/2012 | Kapur et al. |
| 2004/0037091 | A1 | 2/2004 | Guy |
| 2007/0208395 | A1 | 9/2007 | Leclerc et al. |
| 2008/0183053 | A1 | 7/2008 | Borgos et al. |
| 2009/0050812 | A1 | 2/2009 | Dunleavy et al. |
| 2009/0159445 | A1 | 6/2009 | Krishna et al. |
| 2009/0159446 | A1 | 6/2009 | Cui et al. |
| 2009/0159447 | A1 | 6/2009 | Cui et al. |
| 2009/0264036 | A1 | 10/2009 | Yano et al. |
| 2010/0251466 | A1* | 10/2010 | Langley et al. ............ 2/458 |
| 2011/0210856 | A1* | 9/2011 | Beinhocker ............ 340/600 |

OTHER PUBLICATIONS

Briand et al.; "Micro-hotplates on polyimide for sensors and actuators"; Sensors and Actuators A: Physical; 2008; pp. 317-324; vol. 132, No. 8.

Buhr et al.; "Analysis of volatile flavour compounds by Proton Transfer Reaction-Mass Spectrometry: fragmentation patterns and discrimination between isobaric and isomeric compounds"; International Journal of Mass Spectrometry; 2002; pp. 1-7; vol. 221; Elsevier Science B.V.

Courbat et al.; "Evaluation of pH indicator-based colorimetric films for ammonia detection using optical waveguides"; Sensors and Actuators B: Chemical; 2009; pp. 62-70; vol. 143; Elsevier B.V.

Courbat et al.; "Thermal Simulation and Characterization for the Design of Ultra-Low Power Micro-Hotplates on Flexible Substrate"; IEEE Sensors; 2008 Conference; pp. 74-77; IEEE.

"Edmund Optics® Filter Capabilities"; Product Information; 6 pgs.; Edmund Optics Inc.; printed on Nov. 16, 2010; located at www.edmundoptics.com.

"E" Series long wavelength pass filters; 1998; product sheet; one page; located at www.gentexcorp.com.

"Fox-Tek announces smart material tests at NASA successful"; Fiber Optics Weekly Update; Apr. 22, 2005; one page; located at www.fox-tek.com.

"IRC-A1 Carbon Dioxide Infrared Sensor"; Technical Specification; pp. 1-3; located at www.alphasense.com; printed on Aug. 24, 2010.

"IRC-TM NDIR $CO_2$ Transmitter PCB"; Technical Specification; one page; located at www.alphasense.com; printed on Aug. 24, 2010.

Kim et al.; "Waterproof AlInGaP optoelectronics on stretchable substrates with applications in biomedicine and robotics"; Nature Materials; Nov. 2010; pp. 929-937; vol. 9; Macmillan Publishers Limited.

"Larry 2048 & 3000 Series Linear CCD Array Cameras/Detectors"; pp. 1-4; printed on Sep. 21, 2010; located at www.amesphotonics.com.

Lindinger et al.; "Environmental, Food and Medical Applications of Proton-Transfer-Reaction Mass Spectrometry (PTR-MS)"; Advances in Gas-Phase Ion Chemistry; 2001; pp. 1-48; vol. 4; Elsevier Science B.V.

Measures et al.; "Structurally integrated fiber optic damage assessment system for composite materials"; Applied Optics; Jul. 1, 1989; pp. 2626-2633; vol. 28, No. 13: Optical Society of America.

Nyström et al.; "Ultrafast All-Polymer Paper-Based Batteries"; Nano Letters; 2009; pp. 3635-3639; vol. 9, No. 10; American Chemical Society.

Oprea et al.; "Capacitive Gas Sensor Arrays on Plastic Substrates for Low Power and Mobile Applications"; pp. 1431-1434; printed on Sep. 21, 2010.

Oprea et al.; "Integrated Temperature, Humidity and Gas Sensors on Flexible Substrates for Low-Power Applications"; IEEE Sensors; 2007 Conference; pp. 158-161; IEEE.

"Photomultiplier Tubes Basics and Applications"; Hamamatsu; Third Edition; 2008; Cover Page; Table of Contents and pp. 22-27; Hamamatsu Photonics K.K.

Polymer Optical Fiber Specification Sheet; 2007; 4 pgs.; Moritex USA Incorporated.

Potyrailo et al.; "Multianalyte Chemical Identification and Quantitation Using a Single Radio Frequency Identification Sensor"; Anal. Chem.; Jan. 1, 2007; pp. 45-51; vol. 79, No. 1; American Chemical Society.

Qi et al.; "Piezoelectric Ribbons Printed onto Rubber for Flexible Energy Conversion"; Nano Letters; Jan. 26, 2010; pp. 524-528; American Chemical Society.

"Red enhanced Avalanche Photodiode"; Silicon Sensor Specification Sheet; Jan. 27, 2010; pp. 1-2; located at www.silicon-sensor.com.

"Sensitive Real-Time Trace Gas Detector"; product information; pp. 1-2; located at www.PTRMS.com/products; printed on Aug. 24, 2010.

"Si APD array S8550"; production information; Jun. 2006; pp. 1-2; Hamamatsu Photonics K.K.; located at www.hamamatsu.com.

Silicon Sensor PIN Photo Diode Data Sheet; Mar. 9, 2010; pp. 1-3; Silicon Sensor International AG; located at www.silicon-sensor.com.

Tennyson et al.; "Structural Health Monitoring 2005: Advancements and Challenges for Implementation", ed. Fuo-Kuo Chang; pp. 1621-1627, DEStech Publications, Inc., Lancaster, PA, Sep. 12, 2005.

"Ultraviolet (UV) Metal Can LED OUE8A Series"; Optek Technology Inc.; Jul. 2009; production information; pp. 1-8; located at www.optekinc.com.

\* cited by examiner

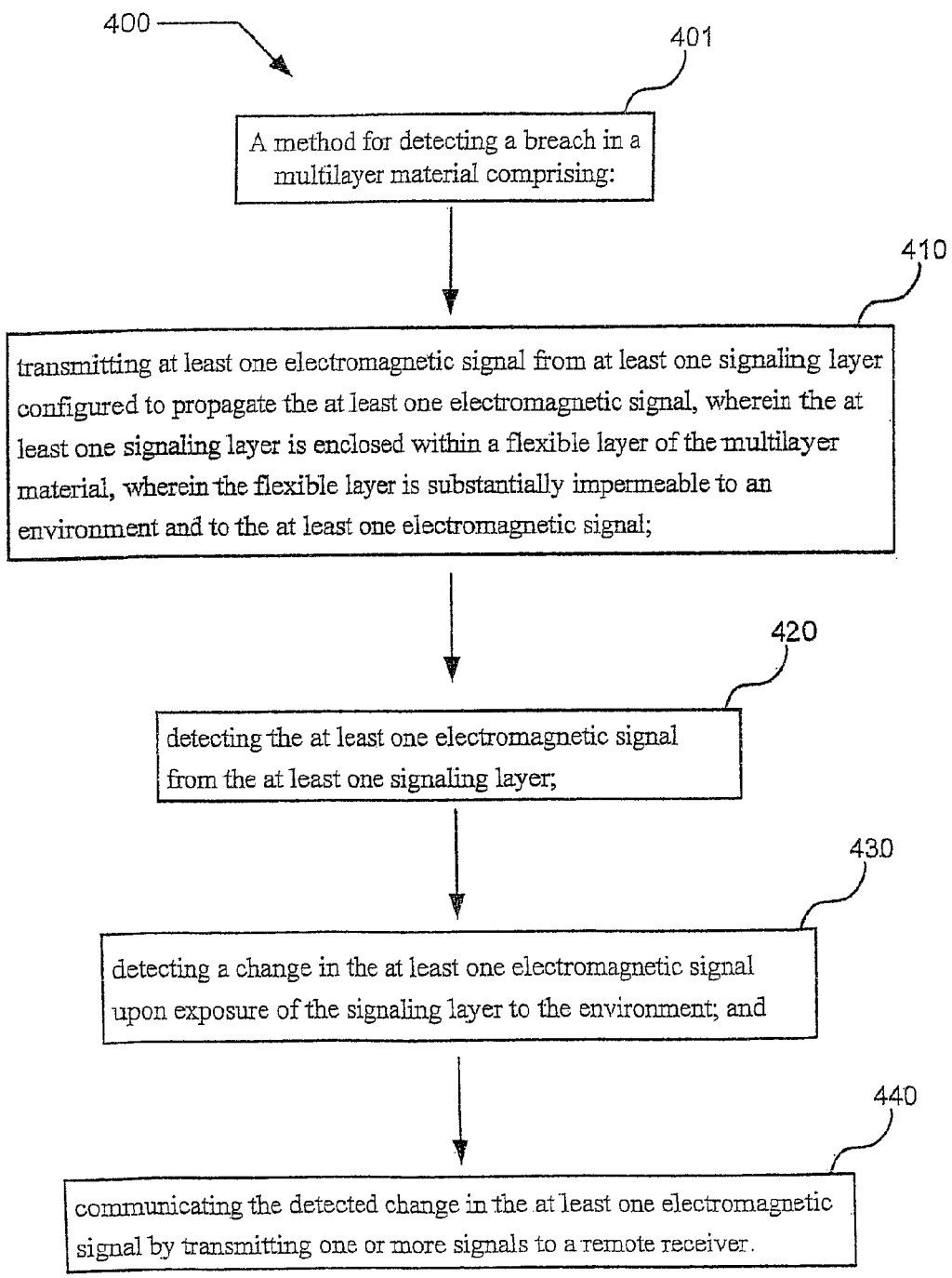

MATERIAL, SYSTEM, AND METHOD THAT PROVIDE INDICATION OF A BREACH

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation of U.S. patent application Ser. No. 12/927,968, entitled MATERIAL, SYSTEM, AND METHOD THAT PROVIDE INDICATION OF A BREACH, naming MAHALAXMI GITA BANGERA, ROY P. DIAZ, RODERICK A. HYDE, MURIEL Y. ISHIKAWA, EDWARD K. Y. JUNG, JORDIN T. KARE, EREZ LIEBERMAN, NATHAN P. MYHRVOLD, DENNIS J. RIVET, MICHAEL A. SMITH, ELIZABETH A. SWEENEY AND LOWELL L. WOOD, JR. as inventors, filed 29 Nov. 2010, which is currently co-pending or is an application of which a currently co-pending application is entitled to the benefit of the filing date.

For purposes of the USPTO extra-statutory requirements, the present application constitutes a continuation-in-part of U.S. patent application Ser. No. 12/927,972, now U.S. Pat. No. 8,501,103, entitled MATERIAL, SYSTEM, AND METHOD THAT PROVIDE INDICATION OF A BREACH naming MAHALAXMI GITA BANGERA, RODERICK A. HYDE, MURIEL Y. ISHIKAWA, EDWARD K. Y. JUNG, JORDIN T. KARE, EREZ LIEBERMAN, NATHAN P. MYHRVOLD, DENNIS J. RIVET, MICHAEL A. SMITH, ELIZABETH A. SWEENEY and LOWELL L. WOOD, JR. as inventors, filed 29 Nov. 2010.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

A flexible multilayer material is described herein that includes a protective, e.g., impermeable or semi-permeable, barrier layer enclosing a signaling layer configured to transmit an electromagnetic (EM) signal indicating a breach in the multilayer material. A detector is configured to detect the EM signal released from the signaling layer of the multilayer material. An article of clothing can include the multilayer material. A system including the multilayer material is configured to transmit a change in the EM signal from the signaling layer to signal to a detector indicating a breach of the multilayer material. The detector can detect a change in the EM signal, including, but not limited to, a decrease, an increase, or an alteration in the EM signal originating from the signaling layer. The detector can detect a decrease or an increase in the intensity of the EM signal. Alternatively or in addition, the detector can detect a change or alteration in the frequency or wavelength of the EM signal. A breach in the multilayer material can cause a decrease in the EM signal from the signaling layer. The decreased EM signal can result from a bend or break in an optical fiber or optical waveguide that is incorporated into the signaling layer. A breach in the multilayer material as part of an article of clothing can result in an increase in the EM signal released from the signaling layer into the environment and detected by the detector on a wall, a floor, or other surface in the environment. The decreased or increased EM signal can activate the detector which is configured to communicate with a receiver and a computing system to notify or warn a wearer of the article of clothing of the need to replace an article of clothing or a glove in the event that the wearer's multilayer material becomes torn or punctured with the result of exposing the wearer to a possibly hazardous material. In a clean room setting, a multilayer material can include a signaling layer that can release an EM signal into the environment, wherein the EM signal can be detected by a detector on a wall, a floor, or other surface in the environment indicating a breach of the multilayer material. The detector can be configured to notify or warn a clean room worker of a possible contamination of the clean room with a hazardous material. Hazardous material can include, but is not limited to, hazardous chemicals, contaminants, pathogens, e.g., bacteria, virus, fungi, or prion. The detector can be configured to contact the multilayer material, and the detector can be configured to directly detect the change in the at least one electromagnetic signal from the signaling layer. The detector can be configured to operate at a distance from the multilayer material, and the detector can be configured to remotely detect the change in the at least one electromagnetic signal from the signaling layer.

In some aspects, a multilayer material is described herein that includes at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. In an embodiment, a multilayer material can include an article of clothing.

An article of clothing is described herein that includes a multilayer material including at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. A change in transmission of the electromagnetic signal from the signaling layer to a detector can indicate a breach of the multilayer material. The electromagnetic signal can include one or more of an ultraviolet signal, a visible light signal and an infrared signal. The signaling layer can include one or more optical threads, optical fibers, or electromagnetic energy waveguides, including optical waveguides. The article of clothing can further include a detector configured to detect a change in the at least one electromagnetic signal from the signaling layer indicating a breach of the multilayer material. In some aspects, the detector can be configured to contact the multilayer material, and the detector can be configured to directly detect the change in the at least one electromagnetic signal from the signaling layer. In some aspects, the detector can be configured to operate at a distance from the multilayer material, and the detector can be configured to remotely detect the change in the at least one electromagnetic signal from the signaling layer. The detector can be configured to operate as a portable unit, a handheld unit, or a unit embedded into walls, furniture, or instruments.

The detector can be configured to measure one or more absolute level of the at least one electromagnetic signal. The detector can be configured to measure a comparison between one or more absolute levels and one or more baseline levels of the at least one electromagnetic signal. The detector can be configured to measure one or more changes of wavelength of the at least one electromagnetic signal. The one or more changes in the at least one electromagnetic signal include, but are not limited to, a change in intensity, a change in phase, difference in polarization state, a change in peak power, or a change in direction of the at least one electromagnetic signal. The detector can be configured to measure one or more wavelength spectra of the at least one electromagnetic signal. The detector can be configured to measure one or more time profiles of the at least one electromagnetic signal. The detector can be configured to store signaling data or metadata on board the detector for future readout. The detector can be configured to transmit one or more signals to a remote receiver. The one or more signals operably coupled to the remote receiver can be wireless. The one or more signals can be delivered by wire or by a physical storage media. The one or more signals to the remote receiver can contain information on one or more of wavelength spectrum of the electromagnetic signal, time profile of the electromagnetic signal, electromagnetic signal magnitude, or electromagnetic signal magnitude compared to baseline. The detector can include at least one of a radio frequency identification sensor and a radio frequency identification reader. The detector can be configured to form a component of the multilayer material. The detector can be configured to be electromagnetically coupled to the signaling layer. The detector can be configured to operate in contact with the multilayer material. The detector can be configured to operate at a distance from the multilayer material. The multilayer material can include at least one of a radio frequency identification sensor and a radio frequency identification reader.

The article of clothing can further include a flexible outer layer configured adjacent to the signaling layer, wherein the flexible outer layer is substantially impermeable to an environment and to the at least one electromagnetic signal. The article of clothing can further include a flexible inner layer configured adjacent to the signaling layer, wherein the flexible inner layer and the flexible outer layer are configured to enclose the signaling layer, and the flexible inner layer is substantially impermeable to an environment and to the at least one electromagnetic signal.

The at least one electromagnetic signal can include one or more of an ultraviolet signal, a visible light signal and an infrared signal. The article of clothing can further include a source of the at least one electromagnetic signal. The article of clothing can further include a power source operably coupled to the source of the at least one electromagnetic signal. The signaling layer can include one or more optical threads or optical fibers. The signaling layer can include one or more electromagnetic energy waveguides. The least one electromagnetic signal can include one or more of a radiofrequency signal, a microwave signal, or a terahertz signal.

The signaling layer can include, but is not limited to, two or more electromagnetic signals that differ in one or more of wavelength spectrum, time profile, intensity, phase, polarization state, peak power, direction, or duty cycle. The signaling layer can include two or more electromagnetic signals that occupy substantially a same location in the signaling layer. The signaling layer can include two or more electromagnetic signals that occupy substantially different locations in the signaling layer. The two or more electromagnetic signals can occupy substantially different locations laterally or vertically in the signaling layer. The detector can further provide metadata to a computing device. The metadata can include, but is not limited to, multilayer material identification, user identification, location of a breach in the multilayer material, detection event time, or multilayer material location. The detector or the remote receiver can be configured to communicate with a computing device. The computing device can be configured to activate a user interface configured to inform one or more of a wearer of the multilayer material, a co-worker, an individual, a supervisor, a safety official, a manufacturer of the multilayer material, a seller of the multilayer material, or an insurance official.

The article of clothing including the multilayer material can further include a second signaling layer including at least one chemical compound. The second signaling layer can include the at least one chemical compound configured to produce at least one gas-phase chemical compound configured to be released into the environment upon exposure of the at least one chemical compound to the environment. The at least one chemical compound can include, but is not limited to, a gas-phase chemical compound, a liquid chemical compound, or a solid chemical compound. The article of clothing including the multilayer material can further include a second detector configured to detect the at least one gas-phase chemical compound or a reaction product thereof in the environment indicating a breach of the multilayer material. The article of clothing including the multilayer material can further include a second remote receiver, wherein the second detector is configured to deliver a second signal to the second remote receiver. The at least one gas-phase chemical compound in the second signaling layer can be configured to diffuse to a second detector. The at least one gas-phase chemical compound can be substantially removed from the environment within a specified time. The second signal to the second remote receiver can include, but is not limited to, data associated with the identity of the at least one gas-phase chemical compound, concentration of the at least one gas-phase chemical compound, comparison of concentration of the at least one gas-phase chemical compound to baseline, or ratio of concentrations of two or more gas-phase chemical compounds. The gas-phase chemical compound can include, but is not limited to, mercaptan, carbon dioxide, 1-hexanol, sulfur hexafluoride, ethanethiol, or furaneol. The at least one chemical compound can be microencapsulated in the signaling layer. The article of clothing including the multilayer material can further include a remote receiver, wherein the remote receiver is configured to receive a signal from a first detector configured to detect a change in the at least one electromagnetic signal from the signaling layer indicating a breach of the multilayer material, and wherein the remote receiver is configured to receive a signal from a second detector configured to detect the at least one gas-phase chemical compound or a reaction product thereof released from the second signaling layer into the environment indicating a breach of the multilayer material.

The article of clothing including the multilayer material can further include an indicator showing presence of the at least one electromagnetic signal within the signaling layer. The article of clothing can include, but is not limited to, a glove, shirt, pant, coverall, apron, shoe covering, or head covering.

A system is described herein that includes a multilayer material including at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. A change in transmission of the electromagnetic signal from the signaling layer to a detector can indicate a breach of the multilayer material. The electromagnetic signal can include one or more of an ultraviolet signal, a visible light signal and an infrared signal. The signaling layer can include one or more optical threads, optical fibers, or electromagnetic energy waveguides, including optical waveguides. The system can further include a detector configured to detect a change in the at least one electromagnetic signal from the signaling layer indicating a breach of the multilayer material. In some aspects, the detector can be configured to contact the multilayer material, and the detector can be configured to directly detect the change in the at least one electromagnetic signal from the signaling layer. In some aspects, the detector can be configured to operate at a distance from the multilayer material, and the detector can be configured to remotely detect the change in the at least one electromagnetic signal from the signaling layer. The detector can be configured to operate as a portable unit, a handheld unit, or a unit embedded into walls, furniture, or instruments.

The detector can be configured to measure one or more absolute level of the at least one electromagnetic signal. The detector can be configured to measure a comparison between one or more absolute levels and one or more baseline levels of the at least one electromagnetic signal. The detector can be configured to measure one or more changes of wavelength of the at least one electromagnetic signal. The one or more changes in the at least one electromagnetic signal include, but are not limited to, a change in intensity, a change in phase, difference in polarization state, a change in peak power, or a change in direction of the at least one electromagnetic signal. The detector can be configured to measure one or more wavelength spectra of the at least one electromagnetic signal. The detector can be configured to measure one or more time profiles of the at least one electromagnetic signal. The detector can be configured to store signaling data or metadata on board the detector for future readout. The detector can be configured to transmit one or more signals to a remote receiver. The one or more signals operably coupled to the remote receiver can be wireless. The one or more signals can be delivered by wire or by a physical storage media. The one or more signals to the remote receiver can contain information on one or more of wavelength spectrum of the electromagnetic signal, time profile of the electromagnetic signal, electromagnetic signal magnitude, or electromagnetic signal magnitude compared to baseline. The detector can include at least one of a radio frequency identification sensor and a radio frequency identification reader. The detector can be configured to form a component of the multilayer material. The detector can be configured to be electromagnetically coupled to the signaling layer. The detector can be configured to operate in contact with the multilayer material. The detector can be configured to operate at a distance from the multilayer material. The multilayer material can include at least one of a radio frequency identification sensor and a radio frequency identification reader.

The system including the multilayer material can further include a flexible outer layer configured adjacent to the signaling layer, wherein the flexible outer layer is substantially impermeable to an environment and to the at least one electromagnetic signal. The system can further include a flexible inner layer configured adjacent to the signaling layer, wherein the flexible inner layer and the flexible outer layer are configured to enclose the signaling layer, and the flexible inner layer is substantially impermeable to an environment and to the at least one electromagnetic signal.

The at least one electromagnetic signal can include one or more of an ultraviolet signal, a visible light signal and an infrared signal. The system can further include a source of the at least one electromagnetic signal. The system can further include a power source operably coupled to the source of the at least one electromagnetic signal. The signaling layer can include one or more optical threads or optical fibers. The signaling layer can include one or more electromagnetic energy waveguides. The least one electromagnetic signal can include one or more of a radiofrequency signal, a microwave signal, or a terahertz signal.

The signaling layer can include, but is not limited to, two or more electromagnetic signals that differ in one or more of wavelength spectrum, time profile, intensity, phase, polarization state, peak power, direction, or duty cycle. The signaling layer can include two or more electromagnetic signals that occupy substantially a same location in the signaling layer. The signaling layer can include two or more electromagnetic signals that occupy substantially different locations in the signaling layer. The two or more electromagnetic signals can occupy substantially different locations laterally or vertically in the signaling layer. The detector can further provide metadata to a computing device. The metadata can include, but is not limited to, multilayer material identification, user identification, location of a breach in the multilayer material, detection event time, or multilayer material location. The detector or the remote receiver can be configured to communicate with a computing device. The computing device can be configured to activate a user interface configured to inform one or more of a wearer of the multilayer material, a co-worker, an individual, a supervisor, a safety official, a manufacturer of the multilayer material, a seller of the multilayer material, or an insurance official.

The system including the multilayer material can further include a second signaling layer including at least one chemical compound. The second signaling layer can include the at least one chemical compound configured to produce at least one gas-phase chemical compound configured to be released into the environment upon exposure of the at least one chemical compound to the environment. The at least one chemical compound can include, but is not limited to, a gas-phase chemical compound, a liquid chemical compound, or a solid chemical compound. The system including the multilayer material can further include a second detector configured to detect the at least one gas-phase chemical compound or a reaction product thereof in the environment indicating a breach of the multilayer material. The system including the multilayer material can further include a second remote receiver, wherein the second detector is configured to deliver a second signal to the second remote receiver. The at least one gas-phase chemical compound in the second signaling layer can be configured to diffuse to a second detector. The at least one gas-phase chemical compound can be substantially removed from the environment within a specified time. The second signal to the second remote receiver can include, but is not limited to, data associated with the identity of the at least one gas-phase chemical compound, concentration of the at least one gas-phase chemical compound, comparison of concentration of the at least one gas-phase chemical compound to baseline, or ratio of concentrations of two or more gas-phase chemical compounds. The gas-phase chemical compound can include, but is not limited to, mercaptan, carbon dioxide, 1-hexanol, sulfur hexafluoride, ethanethiol, or furaneol. The at least one chemical compound can be microencapsulated in the signaling layer. The system including the multilayer material can further include a remote receiver, wherein the remote receiver is configured to receive a signal from a first detector configured to detect a change in the at least one electromagnetic signal from the signaling layer indicating a breach of the multilayer material, and wherein the remote receiver is configured to receive a signal from a second detector configured to detect the at least one gas-phase chemical compound or a reaction product thereof released from the second signaling layer into the environment indicating a breach of the multilayer material.

The system including the multilayer material can further include an indicator showing presence of the at least one electromagnetic signal within the signaling layer. The system including the multilayer material can include, but is not limited to, an article of clothing, a bandage, an enclosure, a surgical drape, a glove box, or a food wrapping.

A multilayer material is described herein that includes at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. A change in transmission of the electromagnetic signal from the signaling layer to a detector can indicate a breach of the multilayer material. The electromagnetic signal can include one or more of an ultraviolet signal, a visible light signal and an infrared signal. The signaling layer can include one or more optical threads, optical fibers, or electromagnetic energy waveguides, including optical waveguides. The multilayer material can further include a detector configured to detect a change in the at least one electromagnetic signal from the signaling layer indicating a breach of the multilayer material. In some aspects, the detector can be configured to contact the multilayer material, and the detector can be configured to directly detect the change in the at least one electromagnetic signal from the signaling layer. In some aspects, the detector can be configured to operate at a distance from the multilayer material, and the detector can be configured to remotely detect the change in the at least one electromagnetic signal from the signaling layer. The detector can be configured to operate as a portable unit, a handheld unit, or a unit embedded into walls, furniture, or instruments.

A method for detecting a breach in a multilayer material is described herein that includes transmitting at least one electromagnetic signal from at least one signaling layer configured to propagate the at least one electromagnetic signal, wherein the at least one signaling layer is enclosed within a flexible layer of the multilayer material, wherein the flexible layer is substantially impermeable to an environment and to the at least one electromagnetic signal; detecting the at least one electromagnetic signal from the at least one signaling layer; and detecting a change in the at least one electromagnetic signal upon exposure of the at least one signaling layer to the environment.

The flexible outer layer can be configured adjacent to the signaling layer, wherein the flexible outer layer is substantially impermeable to an environment and to the at least one electromagnetic signal. The flexible inner layer can be configured adjacent to the signaling layer, wherein the flexible inner layer and the flexible outer layer are configured to enclose the signaling layer, and the flexible inner layer is substantially impermeable to an environment and to the at least one electromagnetic signal. The at least one electromagnetic signal can include one or more of an ultraviolet signal, a visible light signal or an infrared signal. The signaling layer can include one or more optical threads or optical fibers. The signaling layer can include one or more electromagnetic energy waveguides.

The method can further include directly detecting the change in the at least one electromagnetic signal from the signaling layer, wherein a detector is configured to contact the multilayer material. The method can further include remotely detecting the change in the at least one electromagnetic signal from the signaling layer, wherein a detector is configured to operate at a distance from the multilayer material. The detector can be configured to operate as a portable unit, a handheld unit, or a unit embedded into walls, furniture, or instruments. The method can further include detecting one or more absolute level of the at least one electromagnetic signal. The method can further include detecting and comparing one or more absolute levels and one or more baseline levels of the at least one electromagnetic signal. The method can further include detecting one or more changes of wavelength of the at least one electromagnetic signal. Detecting one or more changes in the at least one electromagnetic signal can further include detecting a change in one or more of intensity, a change in phase, difference in polarization state, a change in peak power, or a change in direction of the at least one electromagnetic signal. The method can further include detecting one or more wavelength spectra of the at least one electromagnetic signal. The method can further include detecting one or more time profiles of the at least one electromagnetic signal. The method can further include detecting the change from a baseline in the at least one electromagnetic signal. In some aspects, the baseline can be zero.

The method can further include communicating the detected change in the at least one electromagnetic signal by transmitting one or more signals to a remote receiver. The one or more signals operatively coupled to the remote receiver can be wireless. The method can further include transmitting the one or more signals by wire or by a physical storage media. The method wherein transmitting one or more signals to the remote receiver can further include transmitting two or more electromagnetic signals differing in one or more of wavelength spectrum, time profile, intensity, phase, polarization state, peak power, direction, or duty cycle of the two or more electromagnetic signal. The signal from the detector to the remote receiver can contain information on one or more of wavelength spectrum of the electromagnetic signal, time profile of the electromagnetic signal, electromagnetic signal magnitude, or electromagnetic signal magnitude compared to baseline.

In some aspects, the method can further include identifying the wearer of the multilayer material by detection of the at least one electromagnetic signal. In some aspects, the method can further include identifying a breach location in the multilayer material by detection of one or more characteristics of the at least one electromagnetic signal. The one or more characteristics of the at least one electromagnetic signal can include, but is not limited to, one or more of wavelength spectrum of the electromagnetic signal, time profile of the electromagnetic signal, electromagnetic signal magnitude, or electromagnetic signal magnitude compared to baseline. The method includes detecting the change in the at least one electromagnetic signal and can further include detecting the change with at least one of a radio frequency identification sensor and a radio frequency identification reader. The method can further include releasing at least one gas-phase chemical compound into the environment, the at least one gas-phase chemical compound produced from at least one chemical compound within a second signaling layer of the multilayer material upon exposure of the at least one chemical compound to the environment; wherein the second signaling layer is enclosed within the flexible inner layer and the flexible outer layer of the multilayer material. The at least one chemical compound can include, but is not limited to, a gas-phase chemical compound, a liquid chemical compound, or a solid chemical compound. The at least one gas-phase chemical compound in the second signaling layer can be configured to diffuse to a detector. The gas-phase chemical compound can be substantially removed from the environment within a specified time. The gas-phase chemical compound can include, but is not limited to, mercaptan, carbon dioxide, 1-hexanol, sulfur hexafluoride, ethanethiol, or furaneol. The at least one chemical compound can be microencapsulated in the signaling layer.

The method can further include providing metadata from a detector to a computing device. The metadata can include, but is not limited to, multilayer material identification, user's identification, location of a breach in the multilayer material, detection event time, or multilayer material location. The method can further include communicating from a detector or the remote receiver to a computing device. The method can further include communicating the detected change in the at least one electromagnetic signal and communicating a detected change in the at least one gas-phase chemical compound by transmitting one or more signals to a remote receiver, wherein the remote receiver is configured to receive a signal from a first detector configured to detect a change in the at least one electromagnetic signal from the signaling layer indicating a breach of the multilayer material, and wherein the remote receiver is configured to receive a signal from a second detector configured to detect the at least one gas-phase chemical compound or a reaction product thereof released from the second signaling layer into the environment indicating a breach of the multilayer material.

A system for use on a computer is described herein that includes a non-transient computer-readable medium including instructions for analyzing a signal to a detector indicating a breach of a multilayer material, wherein the multilayer material includes at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment; and a non-transient computer-readable medium including instructions for analyzing metadata provided to the detector. The system can further include instructions for analyzing data from a remote receiver, wherein the remote receiver is configured to receive a transmitted signal from the detector indicating the breach in the multilayer material. The electromagnetic signal can include one or more of an ultraviolet signal, a visible light signal and an infrared signal. The signaling layer can include one or more optical threads, optical fibers, or electromagnetic energy waveguides, including optical waveguides. The system can further include a detector configured to detect a change in the at least one electromagnetic signal from the signaling layer indicating a breach of the multilayer material. In some aspects, the detector can be configured to contact the multilayer material, and the detector can be configured to directly detect the change in the at least one electromagnetic signal from the signaling layer. In some aspects, the detector can be configured to operate at a distance from the multilayer material, and the detector can be configured to remotely detect the change in the at least one electromagnetic signal from the signaling layer. The detector can be configured to operate as a portable unit, a handheld unit, or a unit embedded into walls, furniture, or instruments.

The detector can be configured to measure one or more absolute level of the at least one electromagnetic signal. The detector can be configured to measure a comparison between one or more absolute levels and one or more baseline levels of the at least one electromagnetic signal. The detector can be configured to measure one or more changes of wavelength of the at least one electromagnetic signal. The one or more changes in the at least one electromagnetic signal include, but are not limited to, a change in intensity, a change in phase, difference in polarization state, a change in peak power, or a change in direction of the at least one electromagnetic signal. The detector can be configured to measure one or more wavelength spectra of the at least one electromagnetic signal. The detector can be configured to measure one or more time profiles of the at least one electromagnetic signal. The detector can be configured to store signaling data or metadata on board the detector for future readout. The detector can be configured to transmit one or more signals to a remote receiver. The one or more signals operably coupled to the remote receiver can be wireless. The one or more signals can be delivered by wire or by a physical storage media. The one or more signals to the remote receiver can contain information on one or more of wavelength spectrum of the electromagnetic signal, time profile of the electromagnetic signal, electromagnetic signal magnitude, or electromagnetic signal magnitude compared to baseline. The detector can include at least one of a radio frequency identification sensor and a radio frequency identification reader. The detector can be configured to form a component of the multilayer material. The detector can be configured to be electromagnetically coupled to the signaling layer. The detector can be configured to operate in contact with the multilayer material. The detector can be configured to operate at a distance from the multilayer material. The multilayer material can include at least one of a radio frequency identification sensor and a radio frequency identification reader.

The system including the multilayer material can further include a flexible outer layer configured adjacent to the signaling layer, wherein the flexible outer layer is substantially impermeable to an environment and to the at least one electromagnetic signal. The system can further include a flexible inner layer configured adjacent to the signaling layer, wherein the flexible inner layer and the flexible outer layer are configured to enclose the signaling layer, and the flexible inner layer is substantially impermeable to an environment and to the at least one electromagnetic signal.

The at least one electromagnetic signal can include one or more of an ultraviolet signal, a visible light signal and an infrared signal. The system can further include a source of the at least one electromagnetic signal. The system can further include a power source operably coupled to the source of the at least one electromagnetic signal. The signaling layer can include one or more optical threads or optical fibers. The signaling layer can include one or more electromagnetic energy waveguides. The least one electromagnetic signal can include one or more of a radiofrequency signal, a microwave signal, or a terahertz signal.

The signaling layer can include, but is not limited to, two or more electromagnetic signals that differ in one or more of wavelength spectrum, time profile, intensity, phase, polarization state, peak power, direction, or duty cycle. The signaling layer can include two or more electromagnetic signals that occupy substantially a same location in the signaling layer. The signaling layer can include two or more electromagnetic signals that occupy substantially different locations in the signaling layer. The two or more electromagnetic signals can occupy substantially different locations laterally or vertically in the signaling layer. The detector can further provide metadata to a computing device. The metadata can include, but is not limited to, multilayer material identification, user identification, location of a breach in the multilayer material, detection event time, or multilayer material location. The detector or the remote receiver can be configured to communicate with a computing device. The computing device can be configured to activate a user interface configured to inform one or more of a wearer of the multilayer material, a co-worker, an individual, a supervisor, a safety official, a manufacturer of the multilayer material, a seller of the multilayer material, or an insurance official.

The system including the multilayer material can further include a second signaling layer including at least one chemical compound. The second signaling layer can include the at least one chemical compound configured to produce at least one gas-phase chemical compound configured to be released into the environment upon exposure of the at least one chemical compound to the environment. The at least one chemical compound can include, but is not limited to, a gas-phase chemical compound, a liquid chemical compound, or a solid chemical compound. The system including the multilayer material can further include a second detector configured to detect the at least one gas-phase chemical compound or a reaction product thereof in the environment indicating a breach of the multilayer material. The system including the multilayer material can further include a second remote receiver, wherein the second detector is configured to deliver a second signal to the second remote receiver. The at least one gas-phase chemical compound in the second signaling layer can be configured to diffuse to a second detector. The at least one gas-phase chemical compound can be substantially removed from the environment within a specified time. The second signal to the second remote receiver can include, but is not limited to, data associated with the identity of the at least one gas-phase chemical compound, concentration of the at least one gas-phase chemical compound, comparison of concentration of the at least one gas-phase chemical compound to baseline, or ratio of concentrations of two or more gas-phase chemical compounds. The gas-phase chemical compound can include, but is not limited to, mercaptan, carbon dioxide, 1-hexanol, sulfur hexafluoride, ethanethiol, or furaneol. The at least one chemical compound can be microencapsulated in the signaling layer. The system including the multilayer material can further include a remote receiver, wherein the remote receiver is configured to receive a signal from a first detector configured to detect a change in the at least one electromagnetic signal from the signaling layer indicating a breach of the multilayer material, and wherein the remote receiver is configured to receive a signal from a second detector configured to detect the at least one gas-phase chemical compound or a reaction product thereof released from the second signaling layer into the environment indicating a breach of the multilayer material. The system including the multilayer material can further include an indicator showing presence of the at least one electromagnetic signal within the signaling layer. The system including the multilayer material can include, but is not limited to, an article of clothing, a bandage, an enclosure, a surgical drape, a glove box, or a food wrapping.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 4 depicts a diagrammatic view of one aspect of an embodiment of a method for indicating a breach in a multilayer material.

DETAILED DESCRIPTION

Figure 1:
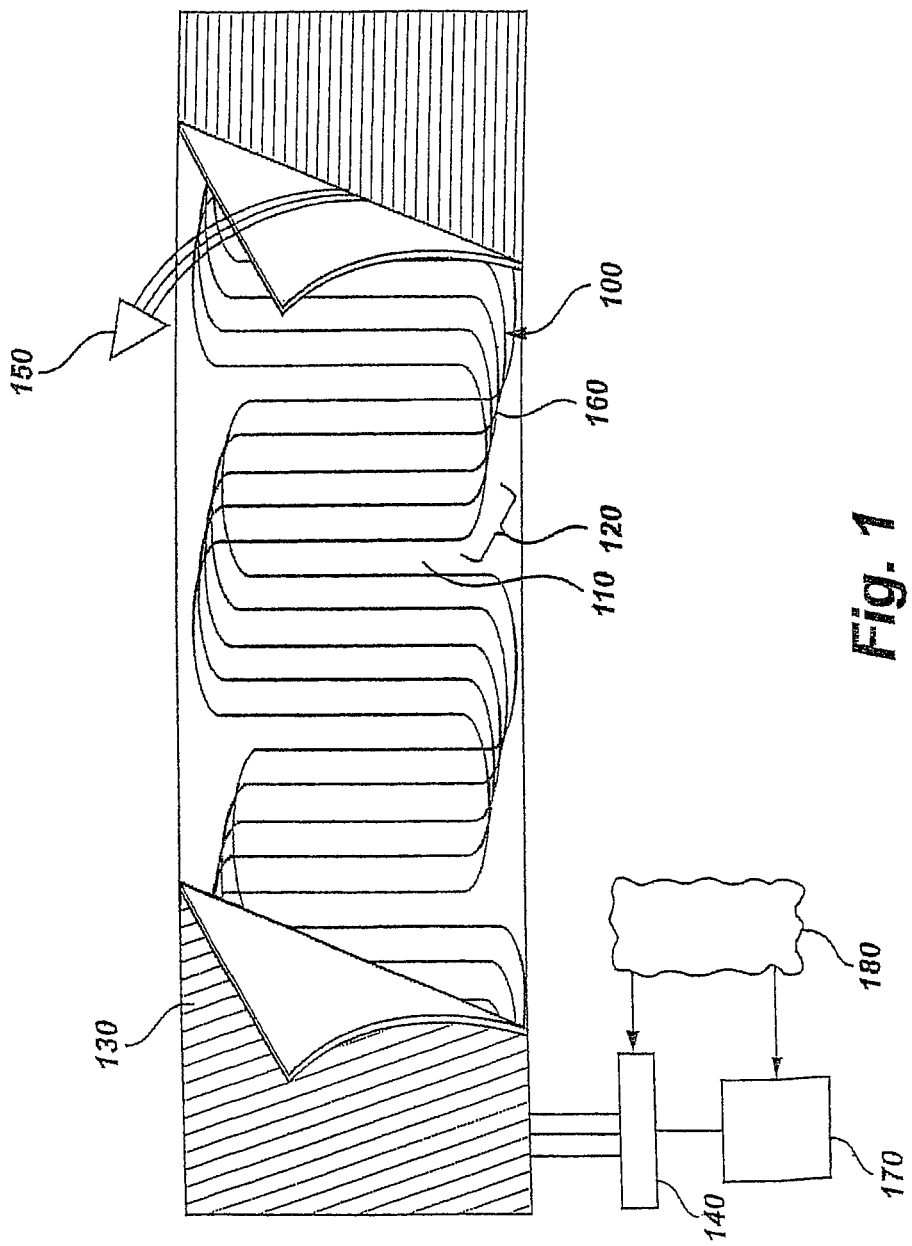
FIG. 1 depicts a diagrammatic view of one aspect of an embodiment of a system including a multilayer material.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

A flexible multilayer material is described herein that includes a protective, e.g., impermeable or semi-permeable, barrier layer enclosing a signaling layer configured to transmit an electromagnetic (EM) signal indicating a breach in the multilayer material. A detector is configured to detect the EM signal released from the signaling layer of the multilayer material. A system including the multilayer material is configured to transmit a change in the EM signal from the signaling layer to signal to a detector indicating a breach of the multilayer material. The detector can detect a change in the EM signal, including, but not limited to, a decrease, an increase, or an alteration in the EM signal originating from the signaling layer. The detector can detect a decrease or an increase in the intensity of the EM signal. Alternatively or in addition, the detector can detect a change or alteration in the frequency or wavelength of the EM signal. A breach in the multilayer material can cause a decrease in the EM signal from the signaling layer. The decreased EM signal can result from a bend or break in an optical fiber or optical waveguide that is incorporated into the signaling layer. A breach in the multilayer material can result in an increase in the EM signal released from the signaling layer into the environment and detected by the detector on a wall, a floor, or other surface in the environment. The decreased or increased EM signal can activate the detector which is configured to communicate with a receiver and a computing system to notify or warn a wearer of the need to replace an article of clothing or a glove in the event that the wearer's multilayer material becomes torn or punctured with the result of exposing the wearer to a possibly hazardous material. In a clean room setting, a multilayer material can include a signaling layer that can release an EM signal into the environment, wherein the EM signal can be detected by a detector on a wall, a floor, or other surface in the environment indicating a breach of the multilayer material. The detector can be configured to notify or warn a clean room worker of a possible contamination of the clean room with a hazardous material. Hazardous material can include, but is not limited to, hazardous chemicals, contaminants, pathogens, e.g., bacteria, virus, fungi, or prion. The detector can be configured to contact the multilayer material, and the detector can be configured to directly detect the change in the at least one electromagnetic signal from the signaling layer. Alternatively, the detector can be configured to operate at a distance from the multilayer material, and the detector can be configured to remotely detect the change in the at least one electromagnetic signal from the signaling layer.

In some aspects, a multilayer material is described herein that includes at least one signaling layer configured to propagate at least one electromagnetic signal; and a flexible layer configured to enclose the at least one signaling layer, wherein the flexible layer is substantially impermeable to an environment and to the at least one electromagnetic signal. The at least one signaling layer is configured to transmit a change in the at least one electromagnetic signal upon exposure of the signaling layer to the environment. In an aspect, a multilayer material can include an article of clothing. An article of clothing is described herein that includes a multilayer material including at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. A change in transmission of the electromagnetic signal from the signaling layer to a detector can indicate a breach of the multilayer material. The electromagnetic signal can include one or more of an ultraviolet signal, a visible light signal and an infrared signal. The signaling layer can include one or more optical threads, optical fibers, or electromagnetic energy waveguides, including optical waveguides. The multilayer material can further include a detector configured to detect a change in the at least one electromagnetic signal from the signaling layer indicating a breach of the multilayer material. The detector can be attached to the multilayer material or separate and remote from the multilayer material, wherein a change in the EM signal resulting from the breach will be detected by the detector.

In some aspects, the system that includes the detector can be configured to transmit a wireless signal to a remote receiver. The detector can transmit metadata related to the identity of the gloves, identity of the individual wearing the gloves, the location of the breach event in the multilayer material, and the date and the time of the breach event. This information can be communicated to the receiver or computing device and stored for future reference.

The multilayer material can further include a second signaling layer including at least one chemical compound. The at least one chemical compound can be configured to produce at least one gas-phase chemical compound configured to be released into the environment upon a breach of the multilayer material and exposure of the at least one chemical compound to the environment. The multilayer material can further include a second, remote detector configured to detect the at least one gas-phase chemical compound or a reaction product thereof in the environment indicating a breach of the multilayer material. The reaction product of the at least one gas-phase chemical compound can be produced by reaction with environmental components including, but not limited to, reactive oxidation in the atmosphere with the gas-phase chemical compound; photoreaction with the gas-phase chemical compound; or reaction of the gas-phase chemical compound with one or more bodily fluids.

A system is described herein that includes a multilayer material including at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. The detector can be attached to the multilayer material or separated from the multilayer material, wherein a change in the EM signal resulting from the breach will be detected by the detector. In some aspects, the detector can be configured to contact the multilayer material, and the detector can be configured to directly detect the change in the at least one electromagnetic signal from the signaling layer. In further aspects, the detector can be configured to operate at a distance from the multilayer material, and the detector can be configured to remotely detect the change in the at least one electromagnetic signal from the signaling layer. In some aspects, the detector can be configured to measure one or more absolute level of the EM signal. In further aspects, the detector is configured to compare one or more absolute level of the EM signal and a baseline level of the EM signal. Generally, a decrease in the EM signal from a baseline level can indicate a breach of the multilayer material. The detector can be configured to measure one or more changes of wavelength of the at least one electromagnetic signal. The one or more changes in the at least one electromagnetic signal can include a change in intensity, a change in phase, difference in polarization state, a change in peak power, or a change in direction of the at least one electromagnetic signal.

A method for detecting a breach in a multilayer material is described herein that includes transmitting at least one electromagnetic signal from at least one signaling layer configured to propagate the at least one electromagnetic signal, wherein the at least one signaling layer is enclosed within a flexible layer of the multilayer material, wherein the flexible layer is substantially impermeable to an environment and to the at least one electromagnetic signal; detecting the at least one electromagnetic signal from the at least one signaling layer; and detecting a change in the at least one electromagnetic signal upon exposure of the at least one signaling layer to the environment.

A system for use on a computer is described herein that includes a non-transient computer-readable medium including instructions for analyzing a signal to a remote detector indicating a breach of a multilayer material, wherein the multilayer material includes at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment; and a non-transient computer-readable medium including instructions for analyzing metadata provided to the detector.

With reference to the figures, and with reference now to FIGS. 1, 2, 3, and 4 depicted is one aspect of a material, an article of clothing, or a system that may serve as an illustrative environment of and/or for subject matter technologies, for example, a multilayer material is described herein that includes at least one signaling layer configured to propagate at least one electromagnetic signal; and a flexible layer configured to enclose the at least one signaling layer, wherein the flexible layer is substantially impermeable to an environment and to the at least one electromagnetic signal. The at least one signaling layer is configured to transmit a change in the at least one electromagnetic signal upon exposure of the signaling layer to the environment. A system can include a multilayer material including at least one signaling layer configured to propagate at least one electromagnetic signal; and a flexible layer configured to enclose the at least one signaling layer, wherein the flexible layer is substantially impermeable to an environment and to the at least one electromagnetic signal, wherein the at least one signaling layer is configured to transmit a change in the at least one electromagnetic signal upon exposure of the signaling layer to the environment. Accordingly, the present disclosure first describes certain specific materials, articles of clothing, systems or methods of FIGS. 1, 2, and 3; and describes embodiments including certain specific materials, articles of clothing, and systems. Those having skill in the art will appreciate that the specific materials, articles of clothing, systems, or methods described herein are intended as merely illustrative of their more general counterparts.

Referring to FIG. 1, depicted is a partial diagrammatic view of one aspect of an embodiment of a multilayer material 100 comprising a flexible inner layer 110 and a flexible outer layer 130 configured adjacent to a flexible layer enclosing a signaling layer 120 including at least one electromagnetic signal 140, wherein the signaling layer 120 is configured to transmit an electromagnetic signal 140 to a detector 150 indicating a breach of the multilayer material 100. The signaling layer 120 can include one or more optical threads or optical fibers 160. A controller 170 and a power supply 180 are provided to control the level of the EM signal passing into the one or more optical threads or optical fibers 160.

Figure 2:
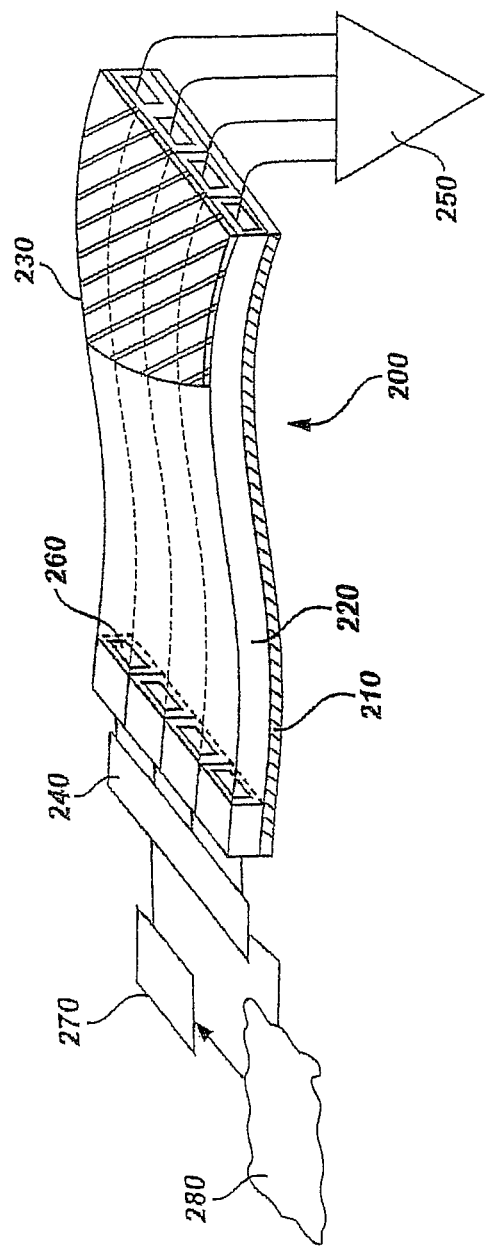
FIG. 2 depicts a diagrammatic view of one aspect of an embodiment of a system including a multilayer material.

Referring to FIG. 2, depicted is a partial diagrammatic view of one aspect of an embodiment of a multilayer material 200 comprising a flexible inner layer 210 and a flexible outer layer 230 configured adjacent to a flexible layer enclosing a signaling layer 220 including at least one electromagnetic signal 240, wherein the signaling layer 220 is configured to transmit an electromagnetic signal 240 to a detector 250 indicating a breach of the multilayer material 200. The signaling layer 220 can include one or more optical waveguides 260. A controller 270 and a power supply 280 are provided to control the level of the EM signal passing into the one or more optical waveguides 260.

Figure 3A:
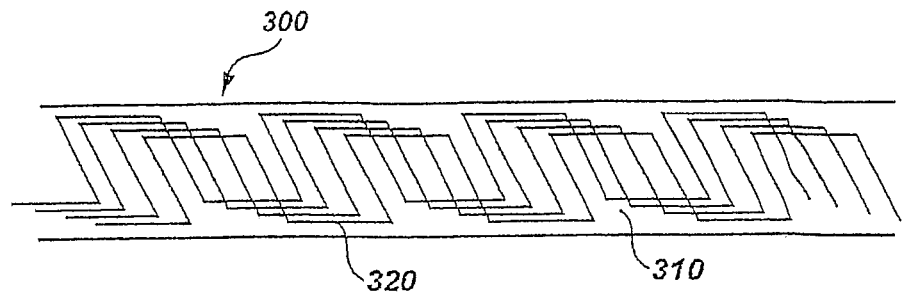
FIGS. 3A, 3B, and 3C depict a diagrammatic view of one aspect of an embodiment of a system including a multilayer material.
Figure 3B:
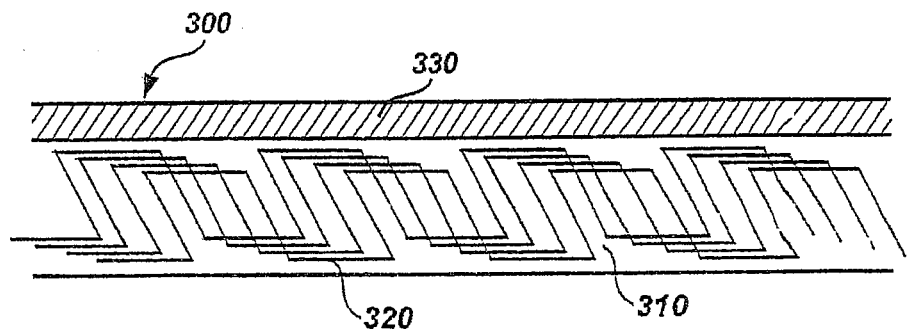
Figure 3C:
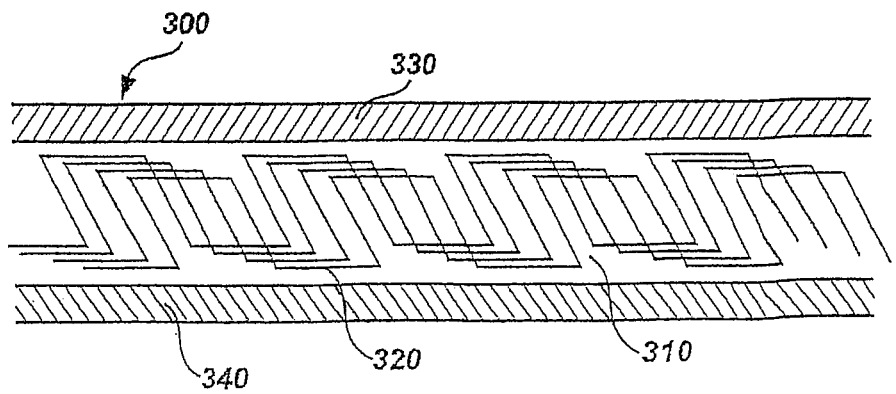

Referring to FIGS. 3A, 3B, and 3C, depicted are aspects of a material, an article of clothing, or a system that may serve as an illustrative environment of and/or for subject matter technologies. Referring to FIG. 3A, depicted is a partial diagrammatic view of one aspect of an embodiment of a multilayer material 300 comprising a flexible layer 310 configured to enclose a signaling layer 320 including at least one electromagnetic signal, wherein the flexible layer is substantially impermeable to an environment and to the at least one electromagnetic signal, and wherein the signaling layer is configured to transmit a change in the at least one electromagnetic signal upon exposure of the signaling layer to the environment. Referring to FIG. 3B, the multilayer material 300 can further include a flexible outer layer 330 configured adjacent to the signaling layer 320, wherein the flexible outer layer 330 is substantially impermeable to an environment and to the at least one electromagnetic signal. Referring to FIG. 3C, the multilayer material 300 can further include a flexible inner layer 340 configured adjacent to the signaling layer 320, wherein the flexible inner layer 340 and the flexible outer layer 330 are configured to enclose the signaling layer 320, and the flexible inner layer 340 is substantially impermeable to an environment and to the at least one electromagnetic signal.

FIG. 4 illustrates a method 400 for detecting a breach in a multilayer material 401 comprising transmitting 410 at least one electromagnetic signal from at least one signaling layer configured to propagate the at least one electromagnetic signal, wherein the at least one signaling layer is enclosed within a flexible layer of the multilayer material, wherein the flexible layer is substantially impermeable to an environment and to the at least one electromagnetic signal; detecting 420 the at least one electromagnetic signal from the at least one signaling layer; detecting 430 a change in the at least one electromagnetic signal upon exposure of the signaling layer to the environment; and communicating 440 the detected change in the at least one electromagnetic signal by transmitting one or more signals to a remote receiver.

Multilayer Material Including a Flexible Inner Layer and a Flexible Outer Layer Configured to Enclose a Signaling Layer Including at Least One Electromagnetic Signal Multilayer materials for gloves or other protective barrier clothing, e.g., impermeable or semi-permeable, can include a flexible inner layer and a flexible outer layer adjacent to a flexible layer that is configured to enclose the at least one signaling layer. The signaling layer includes at least one electromagnetic signal, wherein the at least one signaling layer, the flexible outer layer, and the flexible inner layer are substantially impermeable to an environment and to the at least one electromagnetic signal, and wherein the signaling layer is configured to transmit a change in the at least one electromagnetic signal upon exposure of the signaling layer to the environment. The signaling layer can include one or more of optical threads, optical fibers, or electromagnetic energy waveguides, e.g., optical waveguides. The multilayer material can be constructed and reinforced by one or more processes including, but not limited to, dip forming or spraying cross-linked polyurethane and silicone onto a glove mold. Multilayer material for examination gloves used in industrial laboratories, bioprocessing plants, research laboratories, hospitals, or clinics can be constructed from nitrile by dipping glove forms. Multiple layers of nitrile can be added in a multi-dipping manufacturing process described in U.S. Pat. No. 6,347,408 entitled "Powder-free Gloves Having a Coating Containing Cross-linked Polyurethane and Silicone and Method of Making the Same" issued to Yeh et al. on Feb. 19, 2002; U.S. Pat. No. 5,734,323; "Puncture detecting barrier materials" issued to Hermes et al. on Mar. 31, 1998; U.S. Pat. No. 6,060,986; "Protective glove breach monitoring" issued to Lederer on May 9, 2000, each of which are incorporated herein by reference.

Multilayer material for protective, e.g., impermeable or semi-permeable, gloves or suits can be produced from a variety of materials including, but not limited to, latex, polymers, elastomers, rubber, or plastic. The medical gloves can include a multilayer material comprised of latex or a synthetic polymer, for example, poly (trans-2-chloro-1,3-butadiene), commonly known as poly(chloroprene) (available from DuPont Performance Elastomers L.L.C., Wilmington, Del. 19809).

One or more optical threads, optical fibers, or electromagnetic energy waveguides, e.g., optical waveguides, can be incorporated within a signaling layer of the multilayer material to signal a breach of the protective gloves or protective suits. One or more optical threads, optical fibers, or optical waveguides can be incorporated within and between the layers of multilayer material by mixing the optical fibers with latex or polymer liquids prior to forming (i.e., polymerizing or vulcanizing) a signaling layer of the fabric. For example, methods and compositions for making a multilayer material from a layer of polypropylene that is laminated with a polyethylene film is described in U.S. Pat. No. 7,225,476 entitled "Protective Clothing Against Biological Agents" issued to Cerbini and Lo Ioco on Jun. 5, 2007, which is incorporated herein by reference.

Multi-dipping manufacturing process can be used to form a membrane of multilayer construction that include one or more flexible inner layers, one or more flexible outer layers, and one or more flexible layers configured to enclose the at least one signaling layer which can incorporate the one or more optical threads, optical fibers, or optical waveguides. The one or more flexible layers configured to enclose the signaling layer including one or more optical threads, optical fibers, or optical waveguides can be deformed, ruptured, or pierced to interrupt light flow in the event of a breach of the one or more flexible inner layers or one or more flexible outer layers of the multilayer material. One or more detectors can detect a change from a baseline level in the level of light through the optical threads, optical fibers, or optical waveguides indicating a breach in the multilayer material. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

In an embodiment, gloves constructed of a multilayer material including a flexible inner layer and a flexible outer layer and a flexible layer configured to enclose the at least one signaling layer including at least one electromagnetic signal can provide a flexible protective, e.g., impermeable or semi-permeable, medical glove. The flexible protective medical glove can have a thin glove wall comprising at least one flexible outer layer of a first material having a thickness of between about 1 mil (1 mil=one-thousandth of an inch) to about 40 mils and at least one flexible inner glove layer of a second material having a thickness of between about 0.3 mils to about 30 mils wherein the first material and the second material form the walls of a signaling layer including one or more optical threads, optical fibers, or optical waveguides. The signaling layer including one or more optical threads, optical fibers, or optical waveguides can have a thickness ranging between about 10 mils to about 100 mils, but in some areas of the glove, particularly while the glove is being worn, the signaling layer can become temporarily compressed to less than 1 mil in thickness. Alternatively, or at the same time, the signaling layer in some areas of the glove can be expanded by design or while the glove is being worn can become temporarily expanded to a thickness exceeding 500 mils. At an end or edge of the glove where the hands would be first inserted, the signaling layer can include a detector configured to detect one or more EM signals. The glove can be as flexible as a conventional medical glove, to permit the gloved hand to easily and adequately perform delicate, dexterous, and complex hand work including, for example, the hand work of a surgeon, a medical doctor, a dentist, a laboratory worker, a health care worker, a law enforcement worker, a hospital worker, or others. The glove wall can be constructed from almost any material or combination of materials provided that at least the surface of the inner glove layer and at least the surface of the outer glove layer are liquid-impermeable. The glove wall layers can be made using thin flexible layers of rubber and/or plastic materials. See, e.g., U.S. Pat. No. 5,335,373, entitled "Protective Medical Gloves and Methods for Their Use," which is incorporated herein by reference.

The multilayer material for medical gloves or clean room gloves, as disclosed herein, can be constructed from latex, polyurethane, polyethylene, rubber and other elastomers and polymers by using molds or by dipping or spraying hand forms. For example, multiple layers of latex can be added in a multi-dipping manufacturing process. A membrane formed from liquid latex, solvent cast membranes, liquid polymers, or elastomers can be formed by dip forming, the use of fluidized beds, or spraying the liquid material onto a former. After deposit of one or more flexible inner layers, one or more signaling layers can be deposited. Thereafter, one or more flexible outer layers can be formed, and the membrane can be cured or set according to conventional techniques.

Suitable polymers for use in producing membranes for a multilayer material include prepolymers, i.e., low molecular weight polymers and polymer precursors, prepolymers in combination with polymer precursors dissolved in solvents, liquid monomers, and liquid monomers dissolved in solvents. Specific examples include low molecular weight polymers such as silicone rubber (polydimethyl siloxane: $HO-(Si-(CH_3)_2-O-)_n-H$) with n from 2 to 200; polymer precursors such as low molecular weight diol, e.g., $HO-((CH_2)_4-O)_{18}-H$ and low molecular weight diisocyanate, e.g. $OCN-C_6H_6-CH_2-C_6H_6-NCO$, which when mixed and polymerized form polyurethane. Solvents for low molecular weight polymers include, but are not limited to, xylene and n-hexane. Suitable solvents for polymer precursors include, but are not limited to, dimethyl formamide and dimethyl sulfoxide. Liquid monomers include, but are not limited to, α-alkyl cyanoacrylate, where the alkyl group can be, for example, -methyl, -ethyl, -propyl, or longer alkyl groups. Solvents for liquid monomers include, but are not limited to, dimethyl formamide. Prepolymer, polymer, and polymer precursors include, but are not limited to, mixtures of one or more prepolymers, polymers, or polymer precursors. See, e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 which is incorporated herein by reference.

Multilayer gloves or multilayer clothing using multilayer materials can include, but are not limited to, a structural material including latex rubber, cis-1,4-polyisoprene, cis-polybutadiene, neoprene rubber, nitrile rubber, silicone rubber, cellulose acetate plastic, vinyl plastic, polyethylene plastic, polypropylene plastic, polyvinyl chloride plastic, polyvinyl acetate plastic, polystyrene plastic, polymethyl methyl-acrylate plastic, polyacrylonitrile plastic, vinyllite plastic, vinylidene plastic, polytetrafluoroethylene plastic, polytrifluorochloroethylene plastic, polycaprolactam plastic, polyester plastic, urea formaldehyde plastic, polyurethane plastic, isotactic polypropylene plastic, nylon plastic, rayon plastic, polyamide plastic, phenolic plastic, silicone plastic, silk fiber, cotton fiber, cellulose fiber, wool fiber, animal skin, animal intestinal tissue, animal connective tissue, metallic fiber, mineral fiber and mixtures thereof. See, e.g., U.S. Pat. No. 5,335, 373, which is incorporated herein by reference.

One or more optical threads, optical fibers, or electromagnetic energy waveguides, e.g., optical waveguides, can be incorporated within a flexible layer configured to enclose a signaling layer of the multilayer material to signal when the glove has been breached. One or more optical threads, optical fibers, or optical waveguides can be incorporated within the a flexible layer configured to enclose the signaling layer between the flexible inner layers and flexible outer layers of multilayer material by mixing the optical fibers with latex or polymer liquids prior to dipping the glove formers and adding the next layer. Latex or polymer liquids can be incorporated into a bidirectional fabric with the optical fiber of the signaling layer laid down in a sinuous and/or straight path over the latex or polymer liquid to cover the fingers, palm, back of the hand and wrist of the glove former. For example, methods for making multilayer material with one or more signaling layers or congealing substances are provided. Conventional dipping, spraying or other sheet forming techniques can be used to create one or more flexible-inner layers containing an elastomer material such as latex, solvent cast membranes, liquid polymers or polymer films. Methods of forming the one or more inner layers and one or more outer layers of multilayer material can include: dip coating, spray coating, fluidized bed deposition, vapor deposition, electrical discharge deposition, vacuum deposition, centrifugal coating and extrusion. One or more optical threads, optical fibers, or optical waveguides in a signaling layer can be laid down in a sinuous and/or straight path over the latex or polymer liquid to cover areas of the glove former prior to dipping a glove former into the liquid. One or more flexible layers of latex or polymer can be applied to prevent movement of the one or more optical threads, optical fibers, or optical waveguides present in the latex or polymer layer. One or more flexible inner layers and flexible outer layers of latex or polymer can be applied to the one or more flexible layers configured to enclose the signaling layer. See, e.g., U.S. Pat. No. 5,549,924, entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

A second signaling layer can be created by coating or dipping (with or without a coagulant) latex, liquid polymers, solvent cast membranes or liquid films containing an indicator chemical compound including, but not limited to, a gas-phase chemical compound, a liquid-phase chemical compound, or a solid-phase chemical compound, such as a volatile chemical, aroma, gas, liquid, dye, crystal, or colored agent. Using conventional methods (e.g., dipping, spraying, molding) one or more additional inner flexible layers and outer flexible layers can be added to contain the indicator chemical in the second signaling layer. The second signaling layer including the gas-phase chemical compound, the liquid-phase chemical compound, or the solid-phase chemical compound in the signaling layer is configured upon breach of the multilayer material to diffuse to a remote detector. The signaling compound, e.g., gas-phase chemical compound, the liquid-phase chemical compound, or the solid-phase chemical compound can have a low gaseous half life configured to lower the baseline levels of the chemical signaling compound.

Chemical compounds or gas-phase chemical compounds include volatile compounds that are not corrosive or dangerous to a user, such as mercaptan, carbon dioxide, 1-hexanol, sulfur hexafluoride, ethanethiol, or furaneol, can be incorporated within a flexible inner layer of the medical glove to be released as a gas-phase chemical compound to signal when the glove has been breached. Chemical compounds can be incorporated within and between the flexible inner layers and the flexible outer layers of multilayer material gloves by mixing the chemicals with latex or polymer liquids prior to dipping the glove formers and adding the next layer. For example, methods for making multilayer membranes incorporating one or more signaling layers or congealing substances are provided. Conventional dipping, spraying or other sheet forming techniques can be used to create a flexible inner layer containing an elastomer material such as latex, solvent cast membranes, liquid polymers or polymer films. A second flexible inner layer can be created by coating or dipping (with or without a coagulant) latex, liquid polymers, solvent cast membranes or liquid films containing an indicator chemical such as a volatile chemical, aroma, gas, liquid, dye, crystal, or colored agent. Using conventional methods (e.g., dipping, spraying, molding) one or more additional membrane layers can be added to contain the indicator chemical. Methods of forming the one or more flexible inner layers and the one or more flexible outer layers of multilayer material can include, but are not limited to dip coating, spray coating, fluidized bed deposition, vapor deposition, electrical discharge deposition, vacuum deposition, centrifugal coating and extrusion. Gas-phase chemical compounds, e.g., sulfur hexafluoride, can be infused (bubbled) into the latex or polymer liquid prior to dipping a glove former into the liquid. One or more additional layers of latex or polymer can be applied to prevent diffusion of the sulfur hexafluoride gas present in the latex or polymer layer. See, e.g., U.S. Pat. No. 5,549,924, entitled "Method of Forming A Membrane, Especially A Latex or Polymer Membrane, Including A Deactivating Barrier and Indicating Layer" issued to Shlenker et al. on Aug. 27, 1996, which is incorporated herein by reference.

One or more chemical compounds, e.g., mercaptan, carbon dioxide, 1-hexanol, sulfur hexafluoride, ethanethiol, or furaneol, can be added to the signaling layer between the flexible inner layers and the flexible outer layers of the multilayer material glove by inflating the space between the flexible inner layer and the flexible outer layer with the gas at low pressure. After infusion of the one or more chemical compounds the gas inlet on the glove is sealed. Methods to construct gloves with a sealable gas inlet are described in U.S. Pat. No. 5,911,848 entitled "Method for Making A Puncture Evident Double Layer Surgical Glove" issued to Haber et al. on Jun. 15, 1999; Multilayer gloves with a sealed reservoir between two layers are described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996, each of which are incorporated herein by reference.

Alternatively, one or more chemical compounds, e.g., mercaptan, carbon dioxide, 1-hexanol, sulfur hexafluoride, ethanethiol, or furaneol, can be infused (bubbled) into the polymer liquid of the signaling layer prior to dipping a glove former into the liquid. One or more additional signaling layers and flexible outer layers of polymer liquid are applied to prevent diffusion of the chemical compound, e.g., gas-phase chemical compound, present in the multilayer material of the polymer layer.

Multilayer materials for protective gloves or clothing, e.g., impermeable or semi-permeable, for medical or clean room applications can be used in industrial laboratories, bioprocessing plants, research laboratories, biosafety facilities, hospitals, and clinics. The gloves or clothing are constructed from nitrile, neoprene, or natural rubber by dipping glove forms. Multiple layers and signaling layers of nitrile, neoprene, or natural rubber are added in a multi-dipping manufacturing process described in U.S. Pat. No. 6,347,408 entitled "Powder-free Gloves Having a Coating Containing Cross-linked Polyurethane and Silicone and Method of Making the Same" issued to Yeh et al. on Feb. 19, 2002, which is incorporated herein by reference. A glove former is dipped in a coagulant dispersion comprised of calcium nitrate, calcium carbonate powders, wetting agents and water (or alcohol for alcohol based coagulant dispersion). The coagulant layer deposited on the glove former is allowed to dry. The glove former with the dried coagulant layer is then dipped into a compounded nitrile latex maintained at about 68° F. to about 86° F. The glove former with a first nitrile layer is leached with water for 3 to 10 minutes at 78-110° F. and then dried. The dipping process is repeated to add additional layers of nitrile.

The multilayer material for protective gloves or protective clothing constructed of nitrile, neoprene, or natural rubber can have a thickness of at least about 0.003 inches. The thickness of the multilayer protective gloves or protective clothing can range between about 0.004 inches and about 0.010 inches, or the glove or clothing thickness can range between about 0.005 and about 0.008 inches.

The multilayer material constructed of nitrile, neoprene, or natural rubber can exhibit a tensile strength of greater than about 1300 psi, or greater than about 2000 psi, or greater than about 2600 psi. The stress at 500% of the multilayer material can be less than about 3000 psi, less than about 2000 psi or less than about 1000 psi. The multilayer material can have an elongation to break greater than about 200%, greater than about 400% or greater than about 500%.

The multilayer materials constructed of nitrile, neoprene, or natural rubber can exhibit a dry kinetic coefficient of friction (COF) of less than about 0.5 for the donning (coated) inner surface and greater than about 0.5 for the gripping (uncoated) outer surface. The dry kinetic COF can be less than about 0.4 for the donning surface and greater than about 0.6 for the gripping surface, or the dry kinetic COF can be less than about 0.3 for the donning surface and greater than about 0.7 for the gripping surface.

Natural rubber material coated on their interior with a polyurethane coating can exhibit a tensile strength of greater than about 2000 psi, greater than about 3000 psi, or greater than about 4000 psi. The stress at 500% of the polyurethane coated natural rubber material can be less than about 2000 psi, less than about 1000 psi, or less than about 800 psi. The polyurethane coated natural rubber material can have an elongation to break greater than about 200%, greater than about 500%, or greater than about 800%.

The dry kinetic COF of the polyurethane coated natural rubber material can be less than about 0.5 for the donning surface and greater than about 0.5 for the gripping surface. The dry kinetic COF can be less than about 0.4 for the donning surface and greater than about 0.6 for the gripping surface, or the dry kinetic COF can be less than about 0.3 for the donning surface and greater than about 0.7 for the gripping surface.

Nitrile rubber multilayer material coated on their interior with a polyurethane coating can exhibit a tensile strength of greater than about 2000 psi, greater than about 2500 psi, or greater than about 3000 psi. The stress at 500% of the polyurethane-coated nitrile gloves can be less than about 3000 psi, less than about 2000 psi, or less than about 1000 psi. The polyurethane-coated nitrile multilayer material can have an elongation to break greater than about 200%, greater than about 400%, or greater than about 500%.

The dry kinetic COF of the polyurethane coated nitrile rubber multilayer material can be less than about 0.5 for the donning surface and greater than about 0.4 for the gripping surface. Preferably, the dry kinetic COF can be less than about 0.4 for the donning surface and greater than about 0.6 for the gripping surface, or the dry kinetic COF can be less than about 0.3 for the donning surface and greater than about 0.7 for the gripping surface.

Neoprene rubber multilayer material coated on their interior with the polyurethane coating of the invention can exhibit a tensile strength of greater than about 2000 psi, greater than about 2400 psi, or greater than about 2600 psi. The stress at 500% of the polyurethane coated neoprene gloves can be less than about 2000 psi, less than about 1000 psi, or less than about 800 psi. The polyurethane coated neoprene gloves can have an elongation to break greater than about 200%, greater than about 500%, or greater than about 800%.

The dry kinetic COF of the polyurethane coated neoprene rubber multilayer material can be less than about 0.5 for the donning surface and greater than about 0.5 for the gripping surface. The dry kinetic COF can be less than about 0.4 for the donning surface and greater than about 0.6 for the gripping surface, or the dry kinetic COF can be less than about 0.3 for the donning surface and greater than about 0.7 for the gripping surface. See, e.g., U.S. Pat. No. 6,347,408 entitled "Powder-free Gloves Having a Coating Containing Cross-linked Polyurethane and Silicone and Method of Making the Same" issued to Yeh et al. on Feb. 19, 2002, which is incorporated herein by reference.

A single hand-shaped ceramic mandrel can be used to manufacture a multilayer latex material for surgical glove or surgical clothing configured to include a flexible inner layer and a flexible outer layer configured to enclose the flexible layer configured to enclose the at least one signaling layer including at least one electromagnetic signal, wherein the flexible layer configured to enclose the at least one signaling layer includes one or more optical threads, optical fibers, or optical waveguides. To form the multilayer material, a single layer glove can be formed by first cleaning the mandrel in a wash tank filled with water and detergent. The mandrel can be then moved, as one of a plurality of identical mandrels being carried from station to station by means of a conveyer belt, to a rinse tank where the detergent from the wash tank can be removed. After the mandrel is dried in warm air, it can be dipped in a first coagulant tank containing water and equal amounts of calcium nitrate and calcium carbonate. From the first coagulant tank, the mandrel can be dried in warm air so as to leave the mandrel covered with a powdery mold release agent by which to facilitate the removal of the double layer glove. The mandrel can then be dipped in a first latex filled tank to cover the mold release agent with a first layer of latex.

The mandrel can be dried and heated to vulcanize the latex and thereby form a single layer latex glove.

The mandrel around which the multilayer latex material for the glove can now dipped in a second coagulant tank containing water and about three times more calcium carbonate, by weight, than calcium nitrate. The dip of the mandrel into the second coagulant tank can be relatively shallow compared with the dip into the first coagulant tank so that a region around the cuff of the latex glove will not be covered with mold release agent. The mandrel can be dried in warm air to leave a more effective mold release agent covering the multilayer latex material for the glove, except for the cuff area thereof. A single arm machine can be used to produce a layer including an optical fiber laid down in a sinuous and/or straight path that covers the fingers, palm, back of the hand and wrist of the mandrel. The mandrel can then be dipped in a second latex filled tank so that the first glove, including the cuff area, is now covered with latex. After being dried and heated to vulcanize the second layer of latex, first and second layers latex gloves can be combined to encompass the optical fiber-containing signaling layer, one over the other, which are separated by the mold release agent. Inasmuch as the cuff area of the first (i.e., inner) latex glove is not covered with a mold release agent, a latex-to-latex bond can be established between the cuff areas of the first and second latex gloves in order to hermetically seal the gloves together and form the flexible layer enclosing the at least one signaling layer, including one or more optical threads, optical fibers, or optical waveguides, between the flexible inner layer and the flexible outer layer of the multilayer material for the latex glove. Accordingly, an integral multilayer surgical glove can be formed over the mandrel with the mold release agent preventing the flexible inner layer and the flexible outer layer from sticking together while, at the same time, establishing a channel around the finger area of the composite glove through which air will flow, after the channel is first evacuated, in the event that the flexible outer layer of the latex glove is punctured or torn. A supply of high pressure air can be directed from a series of nozzles that are spaced around the cuff area of the multilayer material glove. Blasts of air from the nozzles simultaneously inflate and blow the now completed double layer glove off the mandrel into a bin. See, e.g., U.S. Pat. No. 5,911,848 entitled "Method for Making A Puncture Evident Double Layer Surgical Glove" issued to Haber et al. on Jun. 15, 1999 which is incorporated herein by reference.

Optical Waveguide in a Signaling Layer

A multilayer material can include a flexible inner layer and a flexible outer layer configured adjacent to a flexible layer configured to enclose the at least one signaling layer including at least one electromagnetic signal, wherein the flexible outer layer is substantially impermeable to an environment and to the at least one electromagnetic signal. The signaling layer can include an optical waveguide layer. The signaling layer including the optical waveguide layer laid down in a sinuous and/or straight path can be added by dipping the glove formers in a composite nanofiber material that contains tricyclodecane dimethacrylate and cellulose fiber. A second coating of black epoxy is added to complete sandwiching the signaling layer including the optical waveguide between a protective barrier layer and additional layers of latex added by sequentially dipping the glove formers in liquid elastomers. A multilayer material for protective, e.g., impermeable or semipermeable, gloves or protective clothing includes one or more flexible inner layers and one or more flexible outer layers that include a synthetic polymer, for example, poly (trans-2-chloro-1,3-butadiene), commonly known as poly(chloroprene) (available from DuPont Performance Elastomers L.L.C., Wilmington, Del. 19809). Disruption of the at least one signaling layer including the thin opaque coating sandwiching the waveguide layer will signal any puncture or breach of the multilayer material by altering the refractive index at the boundary of the waveguide layer and allowing internally reflected light to escape the waveguide. See e.g., U.S. Patent Application 2009/0264036 A1 entitled "Nanofiber Sheet, Process for Producing the Same, and Fiber-Reinforced Composite Material" published on Oct. 22, 2009, which is incorporated herein by reference.

Optical Fiber in a Signaling Layer

A multilayer material can include a flexible inner layer and a flexible outer layer configured adjacent to a flexible layer configured to enclose the at least one signaling layer including at least one electromagnetic signal, wherein the flexible outer layer is substantially impermeable to an environment and to the at least one electromagnetic signal. The flexible inner layer, the flexible outer layer, and the flexible layer configured to enclose the at least one signaling layer can be fabricated using a single arm machine to produce a bidirectional fabric incorporating the optical fiber laid down in a sinuous and/or straight path in the signaling layer that covers the fingers, palm, back of the hand and wrist of the glove former. There are a variety of fabric formation technologies that can provide a signaling layer including a reinforced fabric incorporating one or more optical fibers, optical threads, or optical waveguides incorporated with a latex layer to form a signaling layer within a multilayer material. One method for forming a flexible layer configured to enclose the at least one signaling layer involves forming an adhesively bonded latex layer or fabric scrim. The method for forming a signaling layer substrate including one or more optical fibers, optical threads, or optical waveguides involves forming two sets of warp yarns, an upper set and a lower set, between which a continuous optical thread, optical fiber, or optical waveguide can be laid in a sinuous path.

The yarns of warp sets can be selected from any commercially available yarn, including, but not limited to, spun yarns, multi-filament yarns, or monofilament yarns, which are made of polyester, polyamides, polyolefin, ceramic, fiberglass, basalt, carbon, aramid, metal, or combinations thereof. The warp yarns can additionally be twisted, covered, and/or plied. The warp yarns can optionally be single component or bi-component yarns, such as a sheath-core fiber with a low-melt adhesive material in the sheath. Warp yarns can be either polyester or fiberglass. For both bidirectional and tri-directional scrims, an aspect in which the optical fiber path extends in the machine direction in parallel paths can be obtained by forming a warp beam in which the optical fiber replaces one or many of the conventional warp yarns at whatever spacing is desired. In this manner, optical fibers can be made to traverse the length of the scrim. The optical fiber can be put into the scrim construction in a fairly straight manner to minimize yarn crimp. In an aspect, the optical fiber can be used in combination with non-optical fibers, e.g., fiberglass or polyester, to create a warp yarn set, in which adjacent yarns may be of different types.

Whether the cross-directional yarns are inserted in either the square or tri-axial fabric, they are permanently locked into place in the signaling layer. This is typically accomplished with an adhesive composition. During the initial part of fabric formation, the yarns can be held in place only by friction between overlapping yarns. Typically, the construction can then be transported (a) over rollers directly into a chemical dip that coats the fabric with an adhesive, (b) through a nip (or set of squeeze rolls) to squeeze off excess adhesive, and (c) into an oven or over a set of steam- or oil-heated cans to dry and cure the adhesive. The buffer coating on the optical fiber is preferable for protecting the fiber from manufacturing-induced attenuation caused by pressure damage to the core or cladding at the nip roll. The adhesive used to bind the warp yarns and cross-directional yarns to one another may be chosen from materials such as polyvinyl alcohol (PVOH), acrylic, polyvinyl acetate, polyvinyl chloride, polyvinylidiene chloride, polyacrylate, acrylic latex, styrene butadiene rubber (SBR), EVA, plastisol, or any other suitable adhesive. Further, these yarns optionally can be thermally bonded to form the optical fiber substrate if an appropriate low-melt material is present as part of the yarn system. See, e.g., U.S. Pat. No. 7,630,591, "Optical Fiber Substrate Useful as a Sensor or Illumination Device Component"; U.S. Pat. No. 6,851,844, "Fiber optic fabric with opaque coating for directional light emission", each of which are incorporated herein by reference.

The multilayer material including a flexible inner layer and a flexible outer layer configured adjacent to a flexible layer configured to enclose the at least one signaling layer including at least one electromagnetic signal can include optical fibers woven into the signaling layer. The multilayer material can include optical fibers and non-optical fibers. The optical fibers can include glass, plastic, or combination of both glass and plastic. Any fiber capable of light transmission can be used in the multilayer material. The non-optical fibers can include fiberglass, plastic, carbon, poly paraphenyleneterephthalamide (Dupont™ KEVLAR®), cotton, nylon, polyester, or other fibers. A fiber capable of being woven into a fabric can be used in the multilayer material. The composition and characteristics of a non-optical fiber can be dictated by variables which can include the desired use of the fabric, the composition of the coating, and the desired weave pattern. For example, if the fabric is to be used in the manufacturing of protective safety apparel, the non-optical fibers can include cotton. As another example, if a coating, such as epoxy, is applied after the fabric has been woven, a useful non-optical fiber can be a non-optical fiber matched in color to the epoxy or a non-optical fiber that will adhere to the epoxy. In some aspects, the non-optical fiber can be black color. The non-optical fibers can be structural fibers that can match the composition of the structure to which the fabric is to be adhered. For example, poly-paraphenyleneterephthalamide fibers can be used if the fabric is to be placed on the surface of the multilayer material. Non-optical fibers can be comprised of materials including, but not limited, to fiberglass, poly-paraphenyleneterephthalamide, carbon or cotton.

Optical fibers alone or in combination with non-optical fibers can be woven into the multilayer material. See, e.g., U.S. Pat. No. 4,234,907, which is incorporated herein by reference. The optical fibers can be woven in the weft direction, the warp direction, or both. Because a directional light emission can be in the direction that the light was traveling through the optical fiber when it reached the opening, fabrics comprising optical fibers in both the weft and the warp direction can be used in the multilayer material described herein. By definition, the weft threads are the threads usually carried by the shuttle in weaving, whereas the warp threads extend lengthwise in the loom, crossed by the weft threads. Before or after the optical fibers and the non-optical fibers are woven, a coating can be applied to the optical fibers.

Alternatively, multilayer materials including optical fibers that can be fabricated as an optical grid can sense the size and location of a breach in the signal layer. Optical grids are described in which multilayer materials including a grid of optical fibers can be woven into a base fabric of Kevlar fibers. The fiber-optic sensor grids can determine the location and size of penetration of the Kevlar/optical fiber grid material. See e.g., Measures et al., *Applied Optics*, 28: 2626-2633, 1989; and Tennyson et al., in "Structural Health Monitoring 2005: Advancements and Challenges for Implementation", ed. Fuo-Kuo Chang, pp. 1621-1627, DEStech Publications, Inc., Lancaster, Pa., Sep. 12, 2005; *Fiber Optics Weekly Update*, Apr. 22, 2005; which are incorporated herein by reference. Systems that include a multilayer material including arrays of interconnected, ultrathin inorganic light-emitting diodes and photodetectors can be configured in mechanically optimized layouts on one or more flexible layers of the multilayer material. See, e.g., Kim et al., *Nature Materials*, 9: 929-937, 2010, published online: 17 Oct. 2010, which is incorporated herein by reference.

The coating can be applied to the optical fibers during or after the manufacture of the optical fibers. Methods for applying a coating to an optical fiber can include, but are not limited to, extrusion, casting, reaction injection molding, painting, washing, spraying. The method of applying the coating can depend on variables including the composition of the optical fiber and the composition of the coating. For example, if the optical fibers comprise plastic and the coating comprises epoxy, the painting method can be used in the multilayer material. A method can also depend on the timing of the coating application. For example, if the coating is applied during the manufacturing of the fiber, the extrusion method can be used. In an aspect, if the coating is applied after the optical fibers are woven into a fabric, the spraying method or reaction injection molding can be used in the multilayer material.

The coating applied to the optical fibers in the signaling layer can be an opaque coating. The coating can prevent light from passing through the optical fiber. Light entering one end of an optical fiber can pass out of the other end of the fiber after a portion of the light is lost. The lost portion of light can be light that has diffused through the cladding of the optical fiber. The lost light can result in the length of the optical fiber having a glow. The portion of light that results in the glow is referred to herein as leakage. The opaque coating can prevent the leakage and the resulting glow.

The composition and characteristics of a coating applied to the optical fiber can be dictated by variables that can include the desired use of the fabric, the composition of the optical fibers, and the application method. Coatings that can be used in the multilayer material described herein include, but are not limited to, epoxy, latex, fluoropolymer (TEFLON®) and acrylic. For example, if the coating is applied to optical fibers comprising plastic, the coating can be epoxy. The coating can depend on the composition of the optical fiber and the timing of the coating application. For example, when using plastic optical fibers and applying the coating after the fabric is woven, the coating can include epoxy. In a further aspect, when applying the coating by reaction injection molding during fiber manufacture, the coating can depend on the structure to which the fabric is to be adhered. The coating can be a coating that aids in concealing the fibers. Coatings can include, but are not limited to, epoxy, latex, fluoropolymer, or a combination thereof. See e.g., U.S. Pat. No. 6,851,844 B2 entitled "Fiber Optic Fabric with Opaque Coating for Directional Light Emission" issued Feb. 8, 2005, which is incorporated herein by reference.

Multilayer Material Including Light Source and Power Source

The multilayer material can include a flexible inner layer and a flexible outer layer configured adjacent to a flexible layer configured to enclose the at least one signaling layer including at least one electromagnetic signal, wherein the signaling layer includes one or more optical threads, optical fibers, or optical waveguides. The signaling layer can include one or more light sources flexibly interconnected, a power supply coupled to the one or more light sources and operable to provide power to the one or more light sources, a controller coupled to the one or more light sources and the power supply and operable to control the operation of the light sources. The one or more light sources are connected to one or more optical threads, optical fibers, or optical waveguides of the signaling layer configured to selectively distribute light throughout the multilayer material. The waveguide can, in turn, be comprised completely or partially of silicone rubber. The light source can further include the optical waveguide in combination with one or more optical fibers or one or more optical threads.

In an aspect, a suitable light source can include, but is not limited to, one or more light emitting diodes (LEDs), one or more arc lamps, or one or more laser diodes. The light source can be adapted and configured to direct light to the optical fibers, optical threads, or optical waveguide operatively connected to a controller element and powered by a power supply. The actual dimensions of the multilayer material can be varied and can be dependent upon the type of clothing article that incorporates the optical fibers, optical threads, or optical waveguide of the signaling layer. Additionally, the length, width and depth of the optical fibers, optical threads, or optical waveguide can be varied. The light source emits light at a specific wavelength or alternatively within a range of wavelengths to include visible (400-800 nm) or infrared (800-2000 nm).

The multilayer material can include light sources, e.g., light emitting diodes, light emitting quantum dots, laser diodes, or any other light source commensurate or adaptable to the size, shape, and wearability of the signaling layer within the multilayer material. The arrangement of light sources can be adapted to provide sufficient light over all areas of the portions of the multilayer material intended to transmit light through the signaling layer of the multilayer material. In some aspects, linear and array-like configurations of light sources can be used to achieve the objective of light dispersion. It is also possible to arrange the light sources in any other regular or non-regular pattern such as a circle, where the spacing between each light source may or may not be equivalent. These light sources are also operable by a controller element and a power source. In an aspect, each light source can have a light integrator associated with it that controls the light distribution onto the surface of the article of clothing. See e.g., U.S. Application 2007/0208395, which is incorporated herein by reference.

The multilayer material including a flexible inner layer and a flexible outer layer configured adjacent to a flexible layer configured to enclose the at least one signaling layer including at least one electromagnetic signal, wherein the signaling layer includes one or more optical threads, optical fibers, or optical waveguides can be mounted in a flexible substrate in an x-y plane with the optical fibers running in orthogonal rows and columns and respective detectors at each end. Detection of a breach in the multilayer material can occur over an extended area of the multilayer material. Depending upon the thickness of the multilayer material, a cube of the multilayer material can be made up of successive stacked x-y planes or it can be made up of orthogonally arranged x, y, z direction optical fibers. The 2-D array or the 3-D structure can be embedded in a common flexible substrate. To increase photon capture the optical fibers in the signaling layer can follow a helical or serpentine path through the flexible signaling layer. Due to the losses associated with tight bending radii the number of turns within the flexible substrate can be limited. The optical fibers can traverse the flexible signaling layer in a woven pattern. In some aspects, the optical fibers optical threads, or optical waveguides can be wrapped to make an optical fiber ball around and contained in the flexible signaling layer.

The optical fiber sensor can be provided within a flexible layer configured to enclose the at least one signaling layer of the multilayer material. Two versions of this arrangement include, but are not limited to (1) a hollow optical fiber that is mirrored on the inside with an aluminum coating and the EM signal passing through the internal space in the signaling layer. In this embodiment, incidence of the EM signal causes generation of a photon that is caused to traverse to the end of the optical fiber through total internal reflection of the coating on the inner wall of the optical fiber. The hollow optical fiber can act purely as a structural tube and not as a light guide. (2) In a further embodiment, an optical fiber in the signaling layer is provided with an external mirror coating of aluminum or a suitable optical cladding of refractive index less than that of the optical fiber to support total internal reflection. The EM signal of a similar refractive index to that of the optical fiber wall is contained within the optical fiber. Incidence of EM radiation causes photons to pass to the detectors at the end of the optical fiber by total internal reflection. Breaching the flexible inner layer or the flexible outer layer of the multilayer material will cause the signaling layer including one or more of optical threads, optical fibers, or optical waveguides to deform, bend, or break thus decreasing an amount of light reaching the detector. The optical fibers can be mounted in an x-y plane, in a helical structure, or in a 3-D cube. Similarly, an optical fiber ball can be provided. See e.g., U.S. Application 2009/0050812, which is incorporated herein by reference.

Multilayer Material Including Microchip Detectors

The multilayer material including a flexible inner layer and a flexible outer layer configured adjacent to a flexible layer configured to enclose the at least one signaling layer including at least one electromagnetic signal can be fabricated with a microchip detector, including an optical sensor, located in the cuff area and containing a power supply, optical source, optical detector, and microcircuitry. An optical circuit is created in the glove using a laser diode optical source, fiber optic couplings including one or more optical threads, optical fibers, or optical waveguides, and a PIN photodiode optical detector. A laser diode emitting light at 635 nm wavelength and 1 mWatt power output is available from Thorlabs, Newton, N.J. A PIN photodiode that detects wavelengths near 600 nm and converts photons to an electrical signal with an approximate responsivity of 0.50 A/W (amperes/watt) is available from Silicon Sensor International AG, Berlin, Germany. See Specification Sheet: "PIN Photodiodes Series 5", available from Silicon Sensor International AG, Berlin, Germany, which is incorporated herein by reference. The opposite ends of the optical fiber comprising the signaling layer of the multilayer material can be connected via optic couplings to the laser diode source and the PIN photodiode detector on a microchip. A micro-battery can also be included in the microchip to provide power to the optical sensor microchip. In an aspect, the microchip can contain an integrated circuit that receives electrical signals from the photodiode detector and transmits the electrical signals wirelessly to a computer. See e.g., U.S. Pat. No. 6,850,162 B2 entitled "Communicative Glove Containing Embedded Microchip" issued to Cacioli et al. on Feb. 1, 2005, which is incorporated herein by reference.

A discrete or distributed light sensor operably coupled to the flexible layer and configured to be in contact with the at least one signaling layer of the multilayer material can be used to detect an increase or decrease in an EM signal within the optical threads, optical fibers, or optical waveguides, indicating that the optical threads, optical fibers, or optical waveguides has been compromised, and indicating that the multilayer material has been breached.

The signal from the sensor included in the signaling layer can be a continuous and proportional signal, stepped, or simply irreversibly pass/fail signal, or any combination of these signal types. The signal from the sensor can indicate a measured or estimated breach-indicating parameter according to the amount of change, or rate of change in one or more of the parameters being sensed.

The microchip and sensor, whether or not integrated within the flexible inner layers, flexible outer layers, or signaling layers of the multilayer material as a distributed sensor, or as a discrete sensor, can further include an internal self test mechanism, and, additionally a breach alarm. The alarm can be, for example, a piezoelectric acoustic alarm device similar to a wrist watch alarm integrated into, or onto, the glove. The breach alarm can be communicated to a remote computing device or a user of the multilayer material.

The microchip can also include a power supply. The power supply can be integral to microchip, or it can be external to microchip. Such source of electrical power can be provided by a micro-battery integrated with the glove, or from a capacitor charged by the action of putting on the glove, or from an external electromagnetic induction source or radio wave source. The power supply can include a device for generating sufficient power from an externally applied electromagnetic induction field or radio signal. The power supply can also power the sensor, including a separate sensor signal conditioning microchip, as required. Microchip can include a lithium coin cell micro-battery, e.g., Micropower Battery Co., Miami, Fla., or a thin film battery. See, e.g., U.S. Pat. No. 5,338,625, which is incorporated herein by reference.

The multilayer material including the microchip can be designated to monitor the signal from the sensor. Signal refers to an output from the sensor, which is in response to an external stimulus, e.g., EM stimulus from the signaling layer, and can be representative of a characteristic of the status of the optical threads, optical fibers, or optical waveguides within the signaling layer of the multilayer material being sensed by the sensor. The signal can be representative of more than just one physical characteristic and can include multiple characteristics, e.g., resistance and capacitance or voltage and impedance. The signal can include a signal generated in response to a breach in the multilayer material causing a change in light intensity through the optical threads, optical fibers, or optical waveguides within the signaling layer of the multilayer material.

The optical source can include one or more laser diode optical sources. The optical detector can include a transducer that converts an optical signal into an electrical signal, by generating an electrical current proportional to the intensity of incident optical radiation. The relationship between the input optical radiation and the output electrical current is given by the detector responsivity. Optical detectors suitable for fiber optic systems include, but are not limited to, semiconductor photodiodes; fiber optic couplings; semiconductor positive-intrinsic-negative (PIN) photodiodes; or avalanche photodiodes (APDs), e.g., Si Avalanche Photodiode, from Silicon Sensor International AG, Berlin.

Optical detectors can be located remotely from the multilayer material to detect electromagnetic waves emanating from a breach in the signaling layer of the multilayer material. Optical detectors can be Avalanche Photodiode Arrays (available from Hamamatsu Photonics K.K., Hamamatsu City, Japan) or photomultiplier tubes. Modular photomultiplier tubes with an integrated power supply, operating circuitry and an interface to a computer are available (see e.g., Photomultiplier Handbook from Hamamatsu, which is incorporated herein by reference). To reduce extraneous or background light from striking the optical detectors, the optical detectors include a wavelength pass filter (available from Gentex Corp., Carbondale, Pa.) or a band pass filter available from Edmunds Optics, Barrington, N.J. (see e.g., UV band pass Info Sheet: "Hardcoated Bandpass Filters," which is incorporated herein by reference. The wavelength pass filter or band pass filter will selectively filter wavelengths that reach the optical detector. Optical detectors placed on the walls, ceiling, floors and equipment can wirelessly signal a computer system when light emanating from a breach in the multilayer fabric is detected. Signaling from remote detectors can complement signaling from the optical detectors located within the multilayer fabric and activate an alarm or another warning system.

The microchip can include an embedded algorithm or control logic that controls the method of sensing, monitoring and alarm functions for detecting a breach in the multilayer material. In an aspect, a sensing function for detecting a breach based on light passing through an optical fiber or optical waveguide can be in the form of permanent, integrated, "hard wired" analog circuitry, digital control logic, or a combination thereof. The control logic part can be configured as a software routine or routines programmed onto a read only memory (ROM) component of the microchip. In another aspect, the embedded control logic can be in the form of a one-time programmable (OTP) or re programmable software routine or routines programmed onto an EPROM (erasable programmable read only memory) or EEPROM (electrically erasable programmable read only memory) component of the microchip. In a further aspect, the control logic can be written into the microchip's random access memory (RAM) or other memory at "power up" when the glove is worn, or in the presence of a suitable power source. Alternately, an external programming device, such as a computer, can be used to write the control logic into the microchip's RAM or other memory. The control logic can be separate from the power source if desirable. Other means for providing control to the microchip will be understood by those of ordinary skill in the art. See e.g., U.S. Pat. No. 6,850,162 B2 entitled "Communicative Glove Containing Embedded Microchip" issued to Cacioli et al. on Feb. 1, 2005, which is incorporated herein by reference.

PROPHETIC EXAMPLES

Example 1

A Medical Glove that has an Optical Sensor System that Detects a Glove Breach and Signals Remotely to a Computing Device that Calculates, Communicates and Stores Data of the Breach Event A medical glove is constructed with multilayer material including a flexible inner layer and a flexible outer layer adjacent to a flexible layer that encloses a signaling layer incorporating an optical fiber fabric embedded in the latex material of the glove. The signaling layer includes at least one electromagnetic signal. The multilayer material medical gloves including the signaling layer incorporating the optical fiber fabric detects a breach (e.g., a tear, puncture, abrasion or defect in manufacture) of one or more layers of the glove by blocking or interrupting light flow through the optical fiber embedded in the glove. A change in visible light through the optical fiber signals to a detector to provide notification that a breach of the medical glove has occurred. A computer system connected to the detector associated with the multilayer material medical gloves can notify the health care worker, e.g., by a visible or audible signal, of a breach in the glove that can put the health care worker at risk for infection. The multilayer medical gloves are constructed from latex by dipping hand forms. Multiple layers of latex are added in a multi-dipping manufacturing process described in U.S. Pat. No. 5,549,924 entitled "Method of Forming a Membrane, Especially a Latex or Polymer Membrane, Including a Deactivating Barrier and Indicating Layer" issued to Shlenker et al. on Aug. 27, 1996 which is incorporated herein by reference. A glove former is dipped into a coagulant solution such as calcium carbonate plus nitrate in alcohol, and then into a latex liquid. The glove former with a first latex layer is leached with water, and dried, and then the process is repeated to add additional layers of latex. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference.

The signaling layer incorporating an optical fiber fabric is applied to the glove former after the first inner layers of latex are added to the glove former. The layers incorporating the optical fiber fabric are distributed as a network of optical fibers covering the glove to sense a breach of one or more flexible inner layers or flexible outer layers of the glove. The signaling layer incorporating the optical fiber fabric is manufactured from a single optical fiber 1.0 mm in diameter with an attenuation of approximately 0.15 for 650 nm wavelength light over a distance of 1 meter (available from Moritex U.S.A., Inc., San Jose, Calif.). The optical fiber is composed of a polymethylmethacrylate (PMMA) core and a fluorinated polymer cladding (an outer layer with a lower optical index of refraction than the core) and has a minimum radius of curvature of approximately 17 mm. See, e.g., "Polymer Optical Fiber Specification Sheet", Moritex U.S.A., Inc., San Jose, Calif., which is incorporated herein by reference. A single arm machine is used to produce a bidirectional fabric of the signaling layer with the optical fiber laid down in a sinuous and/or straight path that covers the fingers, palm, back of the hand and wrist of the glove former. See e.g., U.S. Pat. No. 7,630,591 B2 entitled "Optical Fiber Substrate Useful as A Sensor or Illumination Device Component" issued to Allen et al. on Dec. 8, 2009, which is incorporated herein by reference. The glove former coated with a first inner flexible latex layer and a signaling layer of fiber optic fabric is dipped in liquid latex to embed the optical fiber fabric in a outer flexible layer of latex. Additional flexible outer layers including a protective, or impermeable or semi-permeable, barrier layer comprised of latex or a synthetic polymer, for example, poly (trans-2-chloro-1,3-butadiene), commonly known as poly (chloroprene) (available from DuPont Performance Elastomers L.L.C., Wilmington, Del. 19809) is added by dipping. The flexible outer layers are reinforced by adding microfibers to the polymer or latex solution prior to dipping the glove formers. Microfibers for reinforcement include aramids, poly paraphenyleneterephthalamide (Dupont™ KEVLAR®), fiber glass, and nylon. Following dipping, leaching and drying of the flexible outer layers a final layer of latex is added by dipping the glove former in liquid latex.

The glove is fabricated with a powered microchip detector including an optical sensor in the cuff area containing a power supply, optical source, optical detector, and microcircuitry. See e.g., U.S. Pat. No. 6,850,162 B2 entitled "Communicative Glove Containing Embedded Microchip" issued to Cacioli et al. on Feb. 1, 2005, which is incorporated herein by reference. An optical circuit is created in the glove using a laser diode optical source, fiber optic couplings, and a PIN photodiode optical detector. A laser diode emitting light at 635 nm wavelength and 1 mWatt power output is available from Thorlabs, Newton, N.J. A PIN photodiode that detects wavelengths near 600 nm and converts photons to an electrical signal with an approximate responsivity of 0.50 A/W (amperes/watt) is available from Silicon Sensor International AG, Berlin, Germany. See Specification Sheet: "PIN Photodiodes Series 5", available from Silicon Sensor International AG, Berlin, Germany, which is incorporated herein by reference. The opposite ends of the optical fiber comprising the signaling layer within the multilayer material of the medical glove are connected via optic couplings to the laser diode source and the PIN photodiode detector on a powered microchip. A micro-battery is also included in the microchip to provide power to the optical sensor microchip. Moreover, the microchip contains an integrated circuit that receives electrical signals from the photodiode detector and transmits those signals wirelessly to a computer.

A breach in a multilayer material medical glove due to penetration by a surgical scalpel severs or bends one or more segments of the optical fiber embedded in the glove. The breach in one or more layers of the glove causes a reduction in light transmission through the optical fiber embedded in the signaling layer of the glove and a reduction in light transmission reaching the photodiode detector. The severing of the optical fiber is detected as a reduction in electrical current transmitted by the photodiode detector. The reduction in electrical current is detected by the integrated circuitry and a wireless signal is sent to a computing device indicating that a breach in the glove has occurred. The computing device immediately alerts the individual glove user, e.g., by a visible or audible signal, that a breach in the glove has occurred, and the alert is also given to the individuals in the room and to other healthcare workers and safety officials to promote containment of any infectious agents present within the working environment.

Example 2

A Multilayer Medical Glove Including an Optical Waveguide and an Optical Detector Circuit that Detects a Breach of the Glove and Signals a Computing Device to Alert the Individual Wearing the Glove and Healthcare Workers that a Breach has Occurred A medical glove is constructed with a multilayer material including a flexible layer that encloses a signaling layer, wherein the signaling layer incorporates an optical waveguide incorporated into one or more signaling layers of the multilayer material. A waveguide breach detector is incorporated into the gloves on a reusable powered microchip. A breach of the medical gloves caused by the needle puncture of one or more inner layers or outer layers of the multilayer material of the medical gloves punctures one of the layers that include one or more optical waveguides embedded in the signaling layer of the multilayer medical glove and causes a reduction in light transmission by the optical waveguide embedded in the signaling layer of the multilayer medical glove. The detector incorporated into the multilayer medical gloves senses a change in light transmission caused by needle puncture of the optical waveguide. The detector signals a computer device that is suitably programmed to alert the healthcare team, e.g., by a visible or audible signal, that a breach of the medical glove has occurred and prompts immediate action by the healthcare team. The detector is incorporated into a microchip that can be removed from the medical glove and is reusable on a new pair of medical gloves containing a multilayer material including a waveguide signaling layer.

The medical gloves including the multilayer material are constructed from latex by using molds or by dipping or spraying forms. For example, multiple flexible layers of latex are added in a multi-dipping manufacturing process described in U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 which is incorporated herein by reference. A glove former is dipped into a coagulant solution such as calcium carbonate plus nitrate in alcohol, and then into a latex liquid. The glove former with a first inner latex layer is leached with water, and dried, and then the process is repeated to add additional layers. Next a thin opaque coating is added to form the signaling layer by dipping the glove formers in black latex. A signaling layer including the waveguide layer is added by dipping the glove formers in a composite nanofiber material that contains tricyclodecane dimethacrylate and cellulose fiber. See e.g., U.S. Patent Application 2009/264036 A1 entitled "Nanofiber Sheet, Process for Producing the Same, and Fiber-Reinforced Composite Material" published on Oct. 22, 2009, which is incorporated herein by reference. A second coating of black epoxy is added to complete sandwiching the waveguide signaling layer and outer flexible layers include additional layers of latex are added by sequentially dipping the glove formers in liquid elastomers. The medical glove has outer flexible layers comprised of a synthetic polymer, for example, poly (trans-2-chloro-1,3-butadiene), commonly known as poly (chloroprene) (available from DuPont Performance Elastomers L.L.C., Wilmington, Del. 19809). Disruption of the signaling layer, which is the thin opaque coating sandwiching the waveguide layer, will signal any puncture or breach of the gloves by altering the refractive index at the boundary of the waveguide layer and allowing internally reflected light to escape the waveguide. See e.g., U.S. Pat. No. 6,851,844 B2 entitled "Fiber Optic Fabric with Opaque Coating for Directional Light Emission" issued Feb. 8, 2005, which is incorporated herein by reference.

Medical gloves including a multilayer material including a flexible layer that encloses an optical waveguide signaling layer, including an opaque coating on the optical waveguide signaling layer fabricated with a microchip that includes a power source, an optical source, a photodiode detector and microcircuitry to monitor the state of the optical waveguide signaling layer in the medical gloves and to signal changes in the optical circuit that may indicate a breach in the medical gloves. The microchip includes a coin cell micro-battery (3 volts, 1000 mAh (milliampere-hour) nominal capacity available from Micropower Battery Co., Miami, Fla.) and a low current LED lamp (maximum 2.0 volts at 2 mA available from Ralph's Industrial Electronic Supplies, Lafayette, La.) that emits approximately 1.8 mcd (millicandella) at approximately 626 nm. A Si Avalanche photodiode (available from Silicon Sensor International AG, Berlin, Germany) that displays high sensitivity for red visible light (approximately 660 nm wavelength) is incorporated in the microchip. See, e.g., Silicon Sensor Specification Sheet: "Si Avalanche Photodiodes Series 12: Red Enhanced" available from Silicon Sensor International AG, Berlin, Germany, which is incorporated herein by reference. The powered microchip also contains microcircuitry that receives electrical signals from the avalanche photodiode detector and transmits those signals wirelessly to a suitably programmed computer. The microchip is fabricated with an optical interface between the avalanche photodiode and the optical waveguide signaling layer of the medical gloves. A second optical interface on the microchip connects the LED lamp to the optical waveguide signaling layer of the medical gloves. Optical interfaces are constructed from a composite nanofiber material that contains tricyclodecane dimethacrylate and cellulose fiber. The nanofiber material efficiently transmits light. See e.g., U.S. Application No. 2009/0264036 A1 entitled "Nanofiber Sheet, Process for Producing the Same, and Fiber-Reinforced Composite Material" published on Oct. 22, 2009, which is incorporated herein by reference. The microchip with microcircuitry, a power supply, optical elements and optical interfaces are "snapped into place" in the medical gloves containing the optical waveguide signaling layer. The medical gloves are disposable but the microchip is reused by transfer to new medical gloves containing a multilayer material including an optical waveguide signaling layer.

Breach of the medical gloves results in disruption of the opaque coating on the optical waveguide signaling layer and possibly the optical waveguide layer itself. Disruption of the internal reflectivity of the optical waveguide results in an altered photonic signal that is detected by the avalanche photodiode and converted to an electronic signal. The altered electronic signal from the photodiode is detected by microcircuitry on the microchip and transmitted wirelessly to a computing device. The computer is programmed to alert the individual wearing the gloves, coworkers and health and safety officials, e.g., by a visible or audible signal, that a breach of medical gloves has occurred, the location (room) of the breach event and the time of the breach event. Moreover, all data concerning the breach event are stored on the computer for later reference.

Example 3

Examination Gloves for Handling Hazardous Materials that Optically Detect a Breach in the Gloves and Send a Signal to a Computer Indicating that a Breach in the Glove Has Occurred An examination glove is constructed with multilayer material including a flexible inner layer adjacent to a flexible layer that encloses a signaling layer containing an optical fabric that signals a breach (e.g., a tear, puncture, abrasion or defect in manufacture) of the glove. Multilayer material for examination gloves used in industrial laboratories, bioprocessing plants, research laboratories, hospitals, and clinics are constructed from nitrile by dipping glove forms. Multiple layers of nitrile are added in a multi-dipping manufacturing process. See e.g., U.S. Pat. No. 6,347,408 entitled "Powder-free Gloves Having a Coating Containing Cross-linked Polyurethane and Silicone and Method of Making the Same" issued to Yeh et al. on Feb. 19, 2002 which is incorporated herein by reference. A glove former is dipped in a coagulant dispersion comprised of calcium nitrate, calcium carbonate powders, wetting agents and water (or alcohol for alcohol based coagulant dispersion). The coagulant layer deposited on the glove former is allowed to dry. The glove former with the dried coagulant layer is then dipped into a compounded nitrile latex maintained at about 68° F. to about 86° F. The glove former with a first nitrile layer is leached with water for 3 to 10 minutes at 78° F. to 110° F. and then dried. The dipping process is repeated to add additional layers of nitrile. Alternative methods for making multilayer membranes and multilayer gloves are described in U.S. Pat. No. 5,335,373 entitled "Protective Medical Gloves and Methods for Their Use" issued to Dangman et al. on Aug. 9, 1994, which is incorporated herein by reference. The examination glove has a protective barrier layer comprised of a synthetic polymer, for example, poly (trans-2-chloro-1,3-butadiene), commonly known as poly(chloroprene) (available from DuPont Performance Elastomers L.L.C., Wilmington, Del. 19809).

A flexible layer that encloses a signaling layer incorporating an optical fiber fabric is applied to the glove former after the first layer of nitrile is added by dipping. The signaling layer incorporating optical fiber fabric is a distributed network of optical fibers covering the glove. The layer incorporating the optical fiber fabric detects a breach (e.g., a tear, puncture, abrasion or defect in manufacture) of one or more layers of the glove by blocking or interrupting light flow through the optical fiber embedded in the glove. The layer incorporating optical fiber fabric is manufactured from one or more optical fibers 1.0 mm in diameter with an attenuation of approximately 0.15 for 650 nm wavelength light over a distance of 1 meter (available from Moritex U.S.A., Inc., San Jose, Calif.). The optical fiber is composed of a polymethylmethacrylate (PMMA) core and a fluorinated polymer cladding (an outer layer with a lower optical index of refraction than the core) and has a minimum radius of curvature greater than 17 mm. See, e.g., "Polymer Optical Fiber Specification Sheet", Moritex U.S.A., Inc., San Jose, Calif., which is incorporated herein by reference. A single arm machine is used to produce a bidirectional fabric including the signaling layer with the optical fiber laid down in a sinuous and/or straight path that covers the fingers, palm, back of the hand and wrist of the glove former. See e.g., U.S. Pat. No. 7,630,591 B2 entitled "Optical Fiber Substrate Useful as A Sensor or Illumination Device Component" issued to Allen et al. on Dec. 8, 2009, which is incorporated herein by reference. The glove former coated with a first nitrile flexible inner layer and a signaling layer of fiber optic fabric is dipped in liquid nitrile latex to embed the optical fiber fabric in an outer flexible layer of nitrile. Then an additional outer flexible layer including a protective, or impermeable or semi-permeable, barrier layer of poly (trans-2-chloro-1,3-butadiene), commonly known as poly(chloroprene) (available from DuPont Performance Elastomers L.L.C., Wilmington, Del. 19809) may be added by dipping. The protective barrier layer may be reinforced by adding microfibers to the polymer solution prior to dipping the glove formers. Microfibers for reinforcement may include aramids, poly paraphenyleneterephthalamide (Dupont™ KEVLAR®), fiber glass, and nylon. Following dipping, leaching and drying of the protective barrier layer a final layer of nitrile is added by dipping the glove former in liquid nitrile latex.

The examination glove is fabricated with a powered microchip in the cuff area containing a power supply, optical source, optical detector, and microcircuitry. See e.g., U.S. Pat. No. 6,850,162 B2 entitled "Communicative Glove Containing Embedded Microchip" issued to Cacioli et al. on Feb. 1, 2005 which is incorporated herein by reference. The gloves are disposable and the microchip is transferred to a new pair of gloves. An optical circuit is created in the glove using a laser diode optical source, fiber optic couplings and a PIN photodiode optical detector. A laser diode emitting light at 635 nm wavelength and 1 mWatt power output is available from Thorlabs, Newton, N.J.) and a PIN photodiode that detects wavelengths near 600 nm and converts photons to an electrical signal with an approximate responsivity of 0.50 A/W (Amperes/Watt) is available from Silicon Sensor International AG, Berlin, Germany. See Specification Sheet: "PIN Photodiodes Series 5", available from Silicon Sensor International AG, Berlin, Germany, which is incorporated herein by reference. The opposite ends of the optical fiber comprising the optical fabric are connected via optic couplings to the laser diode source and the PIN photodiode detector on the microchip. A micro-battery is also included in the microchip to provide power to the microchip. The microchip contains an integrated circuit that receives electrical signals from the photodiode detector and transmits those signals wirelessly to a computer.

For example, a breach in the examination glove due to a cut causes a reduction in light transmission through the optical fiber in the signaling layer of the multilayer material of the glove. The reduction in light transmission is detected as a reduction in electrical current transmitted by the photodiode detector. The reduction in electrical current is detected by the integrated circuitry and a wireless signal is sent to a computing device programmed to indicate that a breach in the glove may have occurred. The computing device is programmed to immediately alert the individual glove user that a breach in the glove may have occurred. The alert is also given to the individuals in the room and to other workers and safety officials to promote containment of any toxic agents.

Example 4

A Medical Glove that Has Photonic Breach Detector that Signals Remotely when the Glove is Breached to a Computing Device that Receives, Communicates and Stores Data from the Breach Event A medical glove constructed with multiple layers including a flexible inner layer and a flexible outer layer configured adjacent to a flexible layer that encloses a signaling layer incorporating an optical waveguide that signals a breach (e.g., a tear, puncture, abrasion or defect in manufacture) of the glove. Multilayer medical gloves are constructed from polyurethane by dipping hand forms. Multiple layers of polyurethane are added in a multi-dipping manufacturing process. See e.g., U.S. Pat. No. 5,549,924 entitled "Method of Forming A Membrane, Especially A Latex or Polymer Membrane, Including A Deactivating Barrier and Indicating Layer" issued to Shlenker et al. on Aug. 27, 1996 and U.S. Pat. No. 6,347,408 entitled "Powder-free Gloves Having a Coating Containing Cross-linked Polyurethane and Silicone and Method of Making the Same" issued to Yeh et al. on Feb. 19, 2002, each of which are incorporated herein by reference. A glove former is dipped into a coagulant solution such as calcium carbonate plus nitrate in alcohol, and then into a polyurethane dispersion. The process is repeated to add flexible inner layers of polyurethane or other polymers. A signaling layer including an optical waveguide layer is added by dipping the optical waveguide layer in elastomer liquids to form a cladding layer, a core layer and a second cladding layer. A thin cladding layer is added by dipping the glove former in an elastomer liquid (e.g., polysiloxane) then a core layer is added by dipping in polyurethane and then a second thin cladding layer of polysiloxane is added. See e.g., U.S. Patent Application 2008/0183053 A1 entitled "Optical Power Modulation Vital Sign Detection Method and Measurement Device" published on Jul. 31, 2008, which is incorporated herein by reference. The medical glove includes a flexible outer layer including a protective, or impermeable or semi-permeable, barrier layer comprised of a synthetic polymer, for example, poly (trans-2-chloro-1,3-butadiene), commonly known as poly(chloroprene) (available from DuPont Performance Elastomers L.L.C., Wilmington, Del. 19809).

Multilayer fabric medical gloves with a flexible layer that encloses an optical waveguide signaling layer are fabricated with a powered microchip that includes an optical source, a photodiode detector and microcircuitry to monitor the state of the optical waveguide signaling layer in the medical gloves and to signal changes in the optical circuit that may indicate a breach in the medical gloves. For example, a medical glove fabricated with an electronic microchip and a sensor embedded in the cuff area are described in U.S. Pat. No. 6,850,162 B2 entitled "Communicative Glove Containing Embedded Microchip" issued to Cacioli et al. on Feb. 1, 2005, which is incorporated herein by reference. The microchip is empowered by piezoelectric ribbons printed on a flexible polymer that are incorporated in the fingers and palm of the gloves. Lead/zirconium/titanium nanoribbons (500 nm thick) printed onto flexible polydimethylsiloxane (2.5-5 mm thick) convert mechanical energy into electrical energy during hand movements. See, e.g., Qi et al., NanoLetters, Jan. 26, 2010, DOI: 10.1021/nl903377u, which is incorporated herein by reference. The microchip optical source is a low current LED lamp (maximum 2.0 volts at 2 mA available from Ralph's Industrial Electronic Supplies, Lafayette, La.) that emits approximately 1.8 mcd (millicandella) at approximately 626 nm wavelength. A Si Avalanche photodiode (available from Silicon Sensor International AG, Berlin, Germany) that displays high sensitivity for red visible light (approximately 660 nm wavelength) is incorporated in the microchip as an optical detector. See, e.g., Silicon Sensor Specification Sheet: "Si Avalanche Photodiodes Series 12: Red Enhanced" available from Silicon Sensor International AG, Berlin, Germany, which is incorporated herein by reference. The microchip also contains microcircuitry that receives electrical signals from the avalanche photodiode detector and transmits those signals wirelessly to a computer programmed to signal a breach of the multilayer material of the medical glove. The microchip is fabricated with an optical interface between the avalanche photodiode and the optical waveguide signaling layer of the medical gloves. A second optical interface on the microchip connects the LED lamp to the optical waveguide layer of the medical gloves. Optical interfaces are constructed from a nanofiber material that contains tricyclodecane dimethacrylate and cellulose fiber. The nanofiber composite material efficiently transmits light. See e.g., U.S. Application. No. 2009/0264036 A1 entitled "Nanofiber Sheet, Process for Producing the Same, and Fiber-Reinforced Composite Material" published on Oct. 22, 2009 which is incorporated herein by reference. The microchip with microcircuitry, optical elements and optical interfaces is "snapped into place" in the medical gloves containing an optical waveguide signaling layer. The medical gloves are disposable but the powered microchip is reused by transfer to new medical gloves containing an optical waveguide layer.

Multilayer fabric medical gloves with a flexible layer that encloses an optical waveguide signaling layer also include a remote photonic detection system to detect a breach in the gloves. A breach in the waveguide signaling layer results in the escape of light from the waveguide into free space in the room (e.g., operating room) where avalanche photodiode (APD) detectors installed on the ceiling, floor, walls, furniture and other equipment detect light emanating from the breach. Avalanche photodiode arrays with peak sensitivity at approximately 600 nm wavelength and a gain of approximately 100 and a quantum efficiency of approximately 80% are available from Hamamatsu Photonics K.K., Hamamatsu City, Japan (see Si APD array S8550 Spec. Sheet which is incorporated herein by reference). A wavelength pass filter (available from Gentex Corp., Carbondale, Pa.) is fabricated onto the APD detectors to prevent detection of light with wavelengths shorter than approximately 600 nm and allow detection of light (approximately 626 nm wavelength) emanating from a breach in the glove. Light detected by the remote APD detectors is converted to an electrical signal which is transmitted wirelessly to a computing device. Breach of the medical gloves results in disruption of the optical waveguide signaling layer and the escape of light externally, into the room. Disruption of the waveguide results in an altered photonic signal which is detected by the glove APD and converted to an electronic signal. Light emitted from the breach is detected by remote APD detectors placed in the room which also generate an electric signal. The electronic signals from the photodiodes are detected by microcircuitry on the glove microchip and the remote photonic sensors and transmitted wirelessly to a computing device. The computer is programmed to alert the individual wearing the gloves, coworkers and health and safety officials that a breach of medical gloves has occurred, the location (room) of the breach event, and the time of the breach event. Moreover, all data concerning the breach event are stored on the computer for later reference.

Example 5

A Protective Garment with a Photonic Breach Detector to Alert the Wearer and Other Personnel that the Garment Has Been Breached A protective laboratory suit includes multiple layers including a flexible inner layer and a flexible outer layer configured adjacent to a flexible layer that encloses a signaling layer including an optical waveguide layer to sense any breach (e.g., a tear, puncture, abrasion or defect in manufacture) of the laboratory suit. The protective laboratory suit also is equipped with an optical source (e.g., light emitting diode (LED); an optical detector (e.g., a charge coupled device (CCD) and a power supply (e.g., printed paper battery) associated with the signaling layer. The protective laboratory suit is punctured in the posterior region (not visible to the wearer) by a sharp metal edge in the laboratory, potentially exposing the wearer to an infectious agent. Puncture of the protective laboratory suit disrupts the optical waveguide signaling layer of the protective laboratory suit and causes a change in the number of photons striking the CCD detector in the signaling layer. The CCD converts the photon differential to an electronic signal and sends it to integrated circuitry present on the protective suit. Integrated circuitry on the protective suit sends a wireless signal to a computer that is programmed to analyze and store data from the protective suit as well as the date, time, location and identity of the individual wearing the suit. The computer alerts the individual wearing the suit and health and safety authorities that a breach of the protective suit may have occurred and prompts immediate action.

A protective laboratory suit including hat, face mask, long sleeved shirt, pants and booties is constructed of a multilayer material that is comprised of synthetic polymers to form the flexible inner layers and flexible outer layers of the multilayer material. For example, methods and compositions to make a multilayer fabric from a layer of polypropylene that is laminated with a polyethylene film is described in U.S. Pat. No. 7,225,476 entitled "Protective Clothing Against Biological Agents" issued to Cerbini and Lo loco on Jun. 5, 2007 which is incorporated herein by reference. An optical waveguide layer is added as an optical fiber fabric constructed of polymethylmethacrylate optical fibers and polyester. (Available from GDH Co., LTD., Hsin-Chu, Taiwan). A thin opaque coating is added to the Optical waveguide signaling layer by spraying the optical fiber fabric with black latex. Disruption of the thin opaque coating sandwiching the optical waveguide signaling layer will signal any puncture or breach of the suit by altering the refractive index at the boundary of the optical waveguide layer and allowing internally reflected light to escape the optical waveguide. See e.g., U.S. Pat. No. 6,851,844 B2 entitled "Fiber Optic Fabric with Opaque Coating for Directional Light Emission" issued to Guy, James K. on Feb. 8, 2005 which is incorporated herein by reference.

The protective laboratory suit is fabricated with a powered optical sensor chip embedded in the sleeve. The protective suit with an optical waveguide signaling layer bracketed by an opaque coating is fabricated with a microchip that includes a power source, an optical source, a CCD detector and microcircuitry to monitor the state of the optical waveguide signaling layer in the protective suit and to signal changes in the optical circuit that may indicate a breach in the protective suit. A paper battery with a capacity of between 38-50 mAh per gram is connected to power the microchip with platinum foil electrodes. See e.g., Nystrom et al., *Nano Letters* 9: 3635-3639, 2009 which is incorporated herein by reference. The microchip includes a low current LED lamp (maximum 2.0 volts at 2 mA available from Ralph's Industrial Electronic Supplies, Lafayette, La.) that emits approximately 1.8 mcd (millicandella) at approximately 626 nm. A CCD detector is incorporated in the protective suit. A CCD linear array detector with a spectral response from 360 nm to 800 nm wavelength and 2048 active pixels is available from Ames Photonics, Hurst, Tex. See Data Sheet: "LARRY 2048 & 3000 Series Linear CCD Array Cameras/Detectors" available from Ames Photonics, Hurst, Tex., which is incorporated herein by reference). The microchip also Contains microcircuitry that receives electrical signals from the CCD detector and transmits those signals wirelessly to a computer programmed to notify the user of a breach in the multilayer material. The microchip is fabricated with an optical interface between the CCD and the optical waveguide layer of the protective suit. A second optical interface on the microchip connects the LED lamp to the optical waveguide layer of the protective suit. Optical interfaces are constructed from a nanofiber material that contains tricyclodecane dimethacrylate and cellulose fiber. The composite nanofiber material efficiently transmits light. See e.g., U.S. Application No. 2009/0264036 A1 entitled "Nanofiber Sheet, Process for Producing the Same, and Fiber-Reinforced Composite Material" published on Oct. 22, 2009, which is incorporated herein by reference. The powered microchip with microcircuitry, optical elements, and optical interfaces is reused with multiple protective suits containing an optical waveguide signaling layer. The protective suits are disposable.

Breach of the protective suit results in disruption of the opaque coating on the optical waveguide layer and possibly results in disruption of the optical waveguide layer itself. Disruption of the internal reflectivity of the optical waveguide results in an altered photonic signal that is detected by the CCD detector and converted to an electronic signal. The altered electronic signal from the CCD is received by microcircuitry on the microchip and transmitted wirelessly to a computing device. The computing device is programmed to alert the individual wearing the protective suit, coworkers, and health and safety officials that a breach of a protective suit has occurred, and includes metadata such as the location (room) of the breach event and the time of the breach event. Moreover, all data concerning the breach event are stored on the computer for later reference. The microchip may also include a radio-frequency identification (RFID) sensor and a radio-frequency identification (RFID) reader to indicate the identity of the individual wearing the protective suit, the date and the time of the breach event. This information is received by a RFID reader and communicated to the computer and stored for future reference. The optical sensor microchip including a power supply is attached to the protective laboratory suit at the time it is put on, and the microchip is removed and reused with freshly sterilized protective suits or new protective suits. Activation of the optical sensor by installation of the microchip in a protective suit establishes a baseline photonic signal used for reference to any changes in photonic signal that may occur.

Example 6

A Protective Garment with a Photonic Breach Detector to Alert the Wearer and Other Personnel that the Garment Has Been Breached A protective laboratory suit includes multiple layers including a flexible inner layer and a flexible outer layer configured adjacent to a flexible layer that encloses a signaling layer including an optical waveguide layer to sense any breach (e.g., a tear, puncture, abrasion or defect in manufacture) of the laboratory suit. The protective laboratory suit also is equipped with an optical source (e.g., light emitting diode (LED), and a power supply (e.g., printed paper battery) associated with the signaling layer. When the protective laboratory suit is punctured in the posterior region (not visible to the wearer) by a sharp metal edge in the laboratory, the wearer is potentially exposed to an infectious agent. Puncture of the protective laboratory suit disrupts the optical waveguide signaling layer of the protective laboratory suit and allows light to escape into the environment of the room. Remote photodetectors placed on the walls, ceiling, floor and equipment of the laboratory room detect any light released from the breach in the suit. The photodetectors signal wirelessly to a computer that is programmed to analyze and store data from the protective suit as well as the date, time, location and identity of the individual wearing the suit. The computer alerts the individual wearing the suit and health and safety authorities that a breach of the protective suit may have occurred and prompts immediate action.

A protective laboratory suit, including hat, face mask, long sleeved shirt, pants and booties, is constructed of a multilayer material that is comprised of synthetic polymers to form the flexible inner layers and flexible outer layers of the multilayer material. For example, methods and compositions to make a multilayer fabric from a layer of polypropylene that is laminated with a polyethylene film is described in U.S. Pat. No. 7,225,476 entitled "Protective Clothing Against Biological Agents" issued to Cerbini and Lo loco on Jun. 5, 2007 which is incorporated herein by reference. A flexible layer including an optical waveguide layer is added as an optical fiber fabric constructed of polymethylmethacrylate optical fibers and polyester. (Available from GDH Co., LTD., Hsin-Chu, Taiwan). A thin opaque coating is added to the optical waveguide signaling layer by spraying the optical fiber fabric with black latex. Disruption of the thin opaque coating sandwiching the optical waveguide signaling layer will signal any puncture or breach of the suit by allowing internally reflected light to escape the optical waveguide into the room environment. See e.g., U.S. Pat. No. 6,851,844 B2 entitled "Fiber Optic Fabric with Opaque Coating for Directional Light Emission" issued to Guy, James K. on Feb. 8, 2005 which is incorporated herein by reference.

The protective laboratory suit is fabricated with a powered optical source chip embedded in the sleeve. The protective suit with an optical waveguide signaling layer bracketed by an opaque coating is fabricated with a microchip that includes a power source, an optical source and microcircuitry. A paper battery with a capacity of between 38-50 mAh (milliamp hours) per gram is connected to power the microchip with platinum foil electrodes. See e.g., Nystrom et al., *Nano Letters* 9: 3635-3639, 2009 which is incorporated herein by reference. The microchip includes a near UV LED lamp (available from OPTEK Technology Inc., Carrollton, Tex.; see e.g., LED 420 nm Spec Sheet which is incorporated herein by reference) with a minimum optical power output of approximately 5.8 milliwatts at approximately 395-400 nm wavelength. An optical interface on the microchip connects the LED lamp to the optical waveguide layer of the protective suit. Optical interfaces are constructed from a nanofiber material that contains tricyclodecane dimethacrylate and cellulose fiber. The composite nanofiber material efficiently transmits light. See e.g., U.S. Application No. 2009/0264036 A1 entitled "Nanofiber Sheet, Process for Producing the Same, and Fiber-Reinforced Composite Material" published on Oct. 22, 2009, which is incorporated herein by reference. The powered microchip with microcircuitry, optical elements, and optical interfaces is reused with multiple protective suits containing an optical waveguide signaling layer. The protective suits are disposable.

A breach in the waveguide signaling layer results in the escape of light from the waveguide into the laboratory where avalanche photodiode (APD) detectors installed on the ceiling, floor, walls, furniture and other equipment detect light emanating from the breach. Avalanche photodiode arrays with a quantum efficiency of 60% at 420 nm wavelength and a maximal gain of approximately 100 are available from Hamamatsu Photonics K.K., Hamamatsu City, Japan (see APD array S8550 Spec. Sheet which is incorporated herein by reference). A band pass filter (stock #65-072) available from Edmunds Optics, Barrington, N.J.; see UV band pass Info Sheet: "Hardcoated Bandpass Filters" which is incorporated herein by reference) is fabricated onto the APD detectors to allow detection only of light with wavelengths of approximately 400 nm to 405 nm emanating from a breach in the glove. Light detected by the remote APD detectors is converted to an electrical signal which is transmitted wirelessly to a computing device.

The computing device is programmed to alert the individual wearing the protective suit, coworkers, and health and safety officials that a breach of a protective suit has occurred, and includes metadata such as the location within a room of the breach event and the time of the breach event. Moreover, all data concerning the breach event are stored on the computer for later reference. The microchip may also include a radio frequency identification (RFID) sensor and a radio frequency identification (RFID) reader to indicate the identity of the individual wearing the protective suit, the date and the time of the breach event. This information is received by the RFID reader and communicated to the computer and stored for future reference. The optical sensor microchip including a power supply is attached to the protective laboratory suit at the time it is put on, and the microchip is removed and reused with freshly sterilized protective suits or new protective suits.

Each disclosed range of values of dosages or stimulus signal includes all combinations and sub-combinations of range values, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and or firmware.

In a general sense the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for detecting a breach in a multilayer material comprising:
   transmitting at least one electromagnetic signal from at least one signaling layer configured to propagate the at least one electromagnetic signal, wherein the at least one signaling layer is enclosed within a flexible layer of the multilayer material, wherein the flexible layer is substantially impermeable to an environment and to the at least one electromagnetic signal;
   detecting the at least one electromagnetic signal from the at least one signaling layer;
   detecting a change in the at least one electromagnetic signal upon exposure of the at least one signaling layer to the environment; and
   communicating the detected change in the at least one electromagnetic signal by transmitting one or more signals to a remote receiver, wherein transmitting the one or more signals to the remote receiver includes transmitting two or more electromagnetic signals differing in one or more of wavelength spectrum, time profile, intensity, phase, polarization state, peak power, direction, or duty cycle of the two or more electromagnetic signal.

2. The method of claim 1, wherein a flexible outer layer is configured adjacent to the signaling layer, wherein the flexible outer layer is substantially impermeable to an environment and to the at least one electromagnetic signal.

3. The method of claim 2, wherein a flexible inner layer is configured adjacent to the signaling layer, wherein the flexible inner layer and the flexible outer layer are configured to enclose the signaling layer, and the flexible inner layer is substantially impermeable to an environment and to the at least one electromagnetic signal.

4. The method of claim 1, wherein the at least one electromagnetic signal includes one or more of an ultraviolet signal. a visible light signal or an infrared signal.

5. The method of claim 1, wherein the signaling layer includes one or more optical threads or optical fibers.

6. The method of claim 1, wherein the signaling layer includes one or more electromagnetic energy waveguides.

7. The method of claim 1, further including directly detecting the change in the at least one electromagnetic signal from the signaling layer, wherein a detector is configured to contact the multilayer material.

8. The method of claim 1, further including remotely detecting the change in the at least one electromagnetic signal from the signaling layer, wherein a detector is configured to operate at a distance from the multilayer material.

9. The method of claim 8, wherein the detector is configured to operate as a portable unit, a handheld unit, or a unit embedded into walls, furniture, or instruments.

10. The method of claim 1, further including detecting one or more absolute level of the at least one electromagnetic signal.

11. The method of claim 1, further including detecting and comparing one or more absolute levels and one or more baseline levels of the at least one electromagnetic signal.

12. The method of claim 1, further including detecting one or more changes of wavelength of the at least one electromagnetic signal.

13. The method of claim 1, wherein detecting one or more changes in the at least one electromagnetic signal further includes detecting a change in intensity, a change in phase, difference in polarization state, a change in peak power, or a change in direction of the at least one electromagnetic signal.

14. The method of claim 1, further including detecting one or more wavelength spectra of the at least one electromagnetic signal.

15. The method of claim 1, further including detecting one or more time profiles of the at least one electromagnetic signal.

16. The method of claim 1, further including detecting the change from a baseline in the at least one electromagnetic signal.

17. The method of claim 16, wherein the baseline is zero.

18. The method of claim 1, wherein the one or more signals operatively coupled to the remote receiver is wireless.

19. The method of claim 1, further including transmitting the one or more signals by wire or by a physical storage media.

20. The method of claim 1, further including identifying the wearer of the multilayer material by detection of the at least one electromagnetic signal.

21. The method of claim 1, further including identifying a breach location in the multilayer material by detection of one or more characteristics of the at least one electromagnetic signal.

22. The method of claim 21, wherein the one or more characteristics of the at least one electromagnetic signal include one or more of wavelength spectrum of the electromagnetic signal, time profile of the electromagnetic signal, electromagnetic signal magnitude, or electromagnetic signal magnitude compared to baseline.

23. The method of claim 1, wherein the one or more signals from a detector to the remote receiver contains information on one or more of wavelength spectrum of the electromagnetic signal, time profile of the electromagnetic signal, electromagnetic signal magnitude, or electromagnetic signal magnitude compared to baseline.

24. The method of claim 1, wherein detecting the change in the at least one electromagnetic signal includes detecting the change with at least one of a radio frequency identification sensor and a radio frequency identification reader.

25. A method for detecting a breach in a multilayer material comprising:
transmitting at least one electromagnetic signal from at least one signaling layer configured to propagate the at least one electromagnetic signal, wherein the at least one signaling layer is enclosed within a flexible layer of the multilayer material, wherein the flexible layer is substantially impermeable to an environment and to the at least one electromagnetic signal;
detecting the at least one electromagnetic signal from the at least one signaling layer;
detecting a change in the at least one electromagnetic signal upon exposure of the at least one signaling layer to the environment; and
releasing at least one gas-phase chemical compound into the environment, the at least one gas-phase chemical compound produced from at least one chemical compound within a second signaling layer of the multilayer material upon exposure of the at least one chemical compound to the environment; wherein the second signaling layer is enclosed within the flexible inner layer and the flexible outer layer of the multilayer material.

26. The method of claim 25, wherein the at least one chemical compound includes a gas-phase chemical compound, a liquid chemical compound, or a solid chemical compound.

27. The method of claim 26, wherein the at least one gas-phase chemical compound in the second signaling layer is configured to diffuse to a detector.

28. The method of claim 26, wherein the gas-phase chemical compound is substantially removed from the environment within a specified time.

29. The method of claim 26, wherein the gas-phase chemical compound includes mercaptan, carbon dioxide, 1-hexanol, sulfur hexafluoride, ethanethiol, or furaneol.

30. The method of claim 25, wherein the at least one chemical compound is microencapsulated in the signaling layer.

31. The method of claim 1, further including providing metadata from a detector to a computing device.

32. The method of claim 31, wherein the metadata includes multilayer material identification, user's identification, location of a breach in the multilayer material, detection event time, or multilayer material location.

33. The method of claim 1, further including communicating from a detector or the remote receiver to a computing device.

34. The method of claim 25, further including communicating the detected change in the at least one electromagnetic signal and communicating a detected change in the at least one gas-phase chemical compound by transmitting one or more signals to a remote receiver, wherein the remote receiver is configured to receive a signal from a first detector configured to detect a change in the at least one electromagnetic signal from the signaling layer indicating a breach of the multilayer material, and wherein the remote receiver is configured to receive a signal from a second detector configured to detect the at least one gas-phase chemical compound or a reaction product thereof released from the second signaling layer into the environment indicating a breach of the multilayer material.

35. The method of claim 1, wherein the multilayer material includes an article of clothing.

36. The method of claim 35, wherein the article of clothing includes a glove, shirt, pant, coverall, apron, shoe covering, or head covering.

37. The method of claim 1, wherein the multilayer material includes a bandage, an enclosure, a surgical drape, a glove box, or a food wrapping.

* * * * *